(12) United States Patent
Marici

(10) Patent No.: US 12,280,009 B2
(45) Date of Patent: *Apr. 22, 2025

(54) PROTECTOR HOUSING PLASTIC SPIKE WITH FLASH INTENDED FOR DVO LAST DROP EXTRACTION

(71) Applicant: Becton Dickinson and Company Limited, Dun Laoghaire (IE)

(72) Inventor: Paul Paia Marici, Piscataway, NJ (US)

(73) Assignee: Becton Dickinson and Company Limited, Dun Laoghaire (IE)

( * ) Notice: Subject to any disclaimer, the term of this patent is extended or adjusted under 35 U.S.C. 154(b) by 508 days.

This patent is subject to a terminal disclaimer.

(21) Appl. No.: 17/590,357

(22) Filed: Feb. 1, 2022

(65) Prior Publication Data

US 2022/0151871 A1 May 19, 2022

Related U.S. Application Data

(63) Continuation of application No. 16/379,037, filed on Apr. 9, 2019, now Pat. No. 11,266,570.

(Continued)

(51) Int. Cl.
*A61J 1/20* (2006.01)
*A61M 5/162* (2006.01)
*A61M 5/32* (2006.01)

(52) U.S. Cl.
CPC ............ *A61J 1/201* (2015.05); *A61J 1/2068* (2015.05); *A61J 1/2096* (2013.01); *A61J 1/2082* (2015.05);

(Continued)

(58) Field of Classification Search
CPC .......... A61M 2005/3236; A61M 5/162; A61M 5/32; A61M 5/3202; A61M 5/3204;

(Continued)

(56) References Cited

U.S. PATENT DOCUMENTS 4,886,503 A * 12/1989 Miller ................. A61M 5/3216
604/263
5,411,499 A 5/1995 Dudar et al.
(Continued)

FOREIGN PATENT DOCUMENTS

CN 102292270 A 12/2011
CN 103391888 A 11/2013
(Continued)

*Primary Examiner* — Kai H Weng
(74) *Attorney, Agent, or Firm* — The Webb Law Firm

(57) ABSTRACT

A device for transferring fluids in a closed system transfer device using flash for last drop extraction and to reduce coring. The device including a piercing member having a distal end and a proximal end and defining a longitudinal fluid channel. A first opening positioned at the distal end of the piercing member wherein the first opening is in fluid communication with the longitudinal fluid channel. A cover or flash positioned over the first opening. The cover including a pre-cut pattern wherein the cover opens along the pre-cut pattern upon application of a distally directed force from the longitudinal fluid channel. The distal end including the first opening having a steep taper to facilitate last drop extraction.

19 Claims, 24 Drawing Sheets

Related U.S. Application Data

(60) Provisional application No. 62/655,427, filed on Apr. 10, 2018.

(52) U.S. Cl.
CPC ............... *A61M 5/162* (2013.01); *A61M 5/32* (2013.01); *A61M 5/3202* (2013.01); *A61M 5/3204* (2013.01); *A61M 5/3213* (2013.01); *A61M 5/3216* (2013.01); *A61M 5/3219* (2013.01); *A61M 5/322* (2013.01); *A61M 5/3221* (2013.01); *A61M 5/3232* (2013.01); *A61M 5/3234* (2013.01); *A61M 2005/3236* (2013.01); *A61M 5/3286* (2013.01); *A61M 5/329* (2013.01); *A61M 5/3291* (2013.01)

(58) Field of Classification Search
CPC ............... A61M 5/3213; A61M 5/3216; A61M 5/3219; A61M 5/322; A61M 5/3221; A61M 5/3232; A61M 5/3234; A61M 5/3286; A61M 5/329; A61M 5/3291; A61J 1/201; A61J 1/2068; A61J 1/2082; A61J 1/2096
See application file for complete search history.

(56) References Cited

U.S. PATENT DOCUMENTS

| | | |
|---|---|---|
| 5,478,337 A | 12/1995 | Okamoto et al. |
| 5,713,872 A * | 2/1998 | Feuerborn ........... A61M 5/3275 604/263 |
| 5,776,125 A | 7/1998 | Dudar et al. |
| 8,361,408 B2 | 1/2013 | Lynn |
| 8,409,164 B2 | 4/2013 | Fangrow |
| 8,523,838 B2 | 9/2013 | Tornqvist |
| 8,545,476 B2 | 10/2013 | Ariagno et al. |
| 9,919,826 B2 | 3/2018 | Ivosevic et al. |
| 2009/0057258 A1 | 3/2009 | Tornqvist |
| 2011/0290800 A1 | 12/2011 | Teys |
| 2013/0296804 A1* | 11/2013 | Lambert ................. A61M 5/32 604/263 |
| 2013/0299499 A1 | 11/2013 | Elliott |
| 2014/0276578 A1 | 9/2014 | Bullington et al. |
| 2017/0157336 A1 | 6/2017 | Olsen et al. |
| 2019/0307645 A1 | 10/2019 | Marici |

FOREIGN PATENT DOCUMENTS

| | | |
|---|---|---|
| CN | 105744971 A | 7/2016 |
| EP | 3666246 A1 | 6/2020 |
| JP | H475542 U | 7/1992 |
| JP | H09-294809 A | 11/1997 |
| JP | 105310 A | 1/1998 |
| JP | 1015034 A | 1/1998 |
| JP | 10502568 A | 3/1998 |
| JP | 20086066 A | 1/2008 |
| JP | 2016-511083 A | 4/2016 |
| JP | 2016531607 A | 10/2016 |
| JP | 2020-555904 A | 8/2021 |
| WO | 9302724 A1 | 2/1993 |
| WO | 9633769 A1 | 10/1996 |
| WO | 2015042517 A2 | 3/2015 |
| WO | 2018/064206 A1 | 4/2018 |

\* cited by examiner

PROTECTOR HOUSING PLASTIC SPIKE WITH FLASH INTENDED FOR DVO LAST DROP EXTRACTION

CROSS-REFERENCE TO RELATED APPLICATION

The present application is a continuation of U.S. patent application Ser. No. 16/379,037 entitled "Protector Housing Plastic Spike with Flash Intended for DVO Last Drop Extraction" filed Apr. 9, 2019, which claims priority to U.S. Provisional Application Ser. No. 62/655,427 entitled "Protector Housing Plastic Spike with Flash Intended for DVO Last Drop Extraction" filed Apr. 10, 2018, the entire disclosures of each of which are hereby incorporated by reference in their entirety.

BACKGROUND OF THE INVENTION

Field of the Invention

The present invention relates to a spike for use with a closed system transfer device wherein the spike includes a pre-cut flash covering the fluid opening to facilitate last drop extraction and to reduce coring.

Description of Related Art

Medical drugs and solvents are often supplied in glass or plastic containers, such as vials, bottles, or bags, which are sealed by a rubber, plastic or elastomeric bung, stopper, membrane, or puncturable cap. Such sealing members prevent deterioration or contamination of the drug, allow the contents of a container to be mixed by shaking, and prevent the contents of the container from leaking out and contaminating the surroundings. A cannula or a hollow spike comprising a flow channel and an opening that communicates with the flow channel is usually inserted through such a sealing member to supply fluids to the container and to withdraw fluid therefrom.

Conventional devices used for accessing the containers utilize a piercing member that penetrates the sealing member of a container and defines an opening at a distal end of the piercing member. Typically, after the piercing member accesses the vial, the vial is inverted to withdraw the medicament from the container. Once the contents of the fluid container have drained to a level just under the outermost edge of the opening of the piercing member, no more fluid will be able to drain from the fluid container unless the piercing member is withdrawn slightly. Thus, often times the last few drops of the medicament (which may be very expensive and/or toxic) are not fully removed from the container, which results in waste and requires cleaning/disposal of the container. If the piercing member is retracted through the sealing member of the container to remove the remaining medicament in the container, toxic drug or medicament may leak out and contaminate the surrounding environment during such a procedure and non-filtered air containing undesirable particles, such as dust, pollen, or bacteria, may be drawn into the piercing member and contaminate the medicament therein. Accordingly, many conventional devices will be locked to the container or vial after the piercing member fully enters the vial. In some cases, containers are provided with an extra amount of the drug that is to be withdrawn to allow for the fact that not all of the drug will be withdrawn from the container. A user is then able to withdraw the recommended number of doses from the container, but doing so will increase the cost of each container of medical fluid, increase waste, and make cleaning or disposal of the container more complex.

U.S. Pat. No. 9,919,826, owned by Becton, Dickinson and Company Ltd., discloses a close system transfer device for transferring fluid to or from a fluid container having a spike for piercing the container sealing member. The spike includes a first opening for communication with a fluid channel and a second opening for communication with a vent.

Because sealing members are available in a wide variety of configurations, sizes, and thicknesses, it is difficult to design a spike that is suitable for use with a plurality of different sealing members, while optimizing the use of the drug in the vial in a safe and convenient manner. Also, coring of the sealing member often occurs at the time of insertion of the spike through the sealing member of the vial and/or upon initial and repeated penetration of the sealing member with an injector cannula. Therefore, there is a need to design a spike that includes a covering to prevent coring during insertion of the spike and initial and/or repeated penetration by the injector cannula. There is also a need for a spike having a design/shape, such as a slanted orifice, to facilitate last drop withdrawal of the vial contents and a need for a spike having a design/shape that can be used with a variety of stopper sizes/thicknesses.

SUMMARY OF THE INVENTION

In accordance with an aspect of the disclosure, a device for transferring fluids includes a piercing member having a distal end and a proximal end and defining a longitudinal fluid channel. A first opening is positioned at the distal end of the piercing member. The first opening is in fluid communication with the longitudinal fluid channel. A cover or "flash" is positioned over the first opening. The cover includes a pre-cut pattern, so that this cover opens along the pre-cut pattern upon application of a distally directed force from the longitudinal fluid channel. In accordance with the invention, a "flash" is defined as a covering that closes the fluid orifice of the piercing member in a molded configuration.

This distally directed force can be applied via a cannula extending through the fluid channel which comes into contact with the cover and applies a force to the cover causing the cover to break along the pre-cut pattern.

According to one embodiment, the cover can be a membrane that is molded over the first opening. The cover can include at least one molded hinge connecting the cover to the piercing member. According to a further embodiment, the pre-cut pattern can include a cut along a center portion of the cover dividing the cover into a first portion and a second portion and the at least one molded hinge can comprise a first hinge for securing the first cover portion to a first portion of the piercing member and a second hinge for securing the second cover portion to a second portion of the piercing member at a location opposite from the first portion of the piercing member. During use, upon the application of the distally directed force, the cover opens along the first and second hinges in an outward direction with respect to the first opening.

According to one embodiment, the at least one molded hinge and/or the first and second hinges comprise a living hinge and the cover remains attached to the piercing member via the at least one molded hinge and/or the first and second hinges.

The pre-cut pattern can comprise a cut that partially surrounds the opening, with the exception of the first and second portions, so that during use, the cover remains attached to the piercing member via the first and second hinges.

The distal end of the piercing member including the first opening can include a steep taper to facilitate last drop withdrawal from a container having a sealing member, wherein the steep taper of the piercing member is configured for use with a variety of thicknesses of sealing members.

The piercing member defines a longitudinal vent channel and defines a second opening at the distal end of the piercing member and the device for transferring fluids further comprises a body extending from the proximal end of the piercing member, wherein the body includes a first connecting portion configured to receive a mating connector and a second connecting portion configured to secure the body to a container. The device further includes a pressure equalization arrangement in fluid communication with the longitudinal vent channel of the piercing member.

The first opening of the piercing member extends longitudinally from the distal end of the piercing member. A length of the first opening of the piercing member in a direction extending from the proximal end of the piercing member to the distal end of the piercing member ensures that at least a portion of the first opening of the piercing member is located adjacent an innermost side of a sealing member of a fluid container when the piercing member has penetrated the sealing member.

According to one embodiment, the piercing member can have a cylindrical shape with a pointed tip at the distal end. According to a further embodiment, the piercing member can comprise a first flat portion defining a first planar surface and a second flat portion defining a second planar surface, wherein the first and second flat portions are configured to reduce a penetration force required to pierce a sealing member of a fluid container relative to a piercing member not having the first and second flat portions.

In accordance with another aspect of the disclosure, a device for transferring fluids includes a body having a first side and a second side. A piercing member extends from the second side of the body, wherein the piercing member has a distal end and a proximal end defining a longitudinal fluid channel. At least one opening is positioned at the distal end of the piercing member and the at least one opening is in fluid communication with the longitudinal fluid channel. A cover is positioned over the first opening. The cover includes a pre-cut pattern, wherein the cover opens along the pre-cut pattern upon application of a distally directed force from the longitudinal fluid channel.

According to one embodiment, the cover comprises a membrane that is molded over the first opening and the pre-cut pattern comprises a cut along a center portion of the cover dividing the cover into a first portion and a second portion. The cover also includes a first hinge for securing the first cover portion to a first portion of the piercing member, and a second hinge for securing the second cover portion to a second portion of the piercing member, at a location opposite from the first portion of the piercing member. Upon penetration by the distally directed force, the cover opens along the first and second hinges in an outward direction with respect to the first opening. In order to facilitate this opening, the pre-cut pattern comprises a cut that partially surrounds the opening, with the exception of the first and second portions, so that the cover remains attached to the piercing member via the first and second hinges. The distal end of the piercing member that includes the first opening has a steep taper to facilitate last drop withdrawal from a container having a sealing member, wherein the steep taper of the piercing member is configured for use with a variety of thicknesses of sealing members.

The piercing member also defines a longitudinal vent channel and defines a second opening at the distal end of the piercing member. The body of the fluid transfer device extends from the proximal end of the piercing member. The body includes a first connecting portion configured to receiving a mating connector and a second connecting portion configured to secure the body to a container.

DETAILED DESCRIPTION

Figure 1:
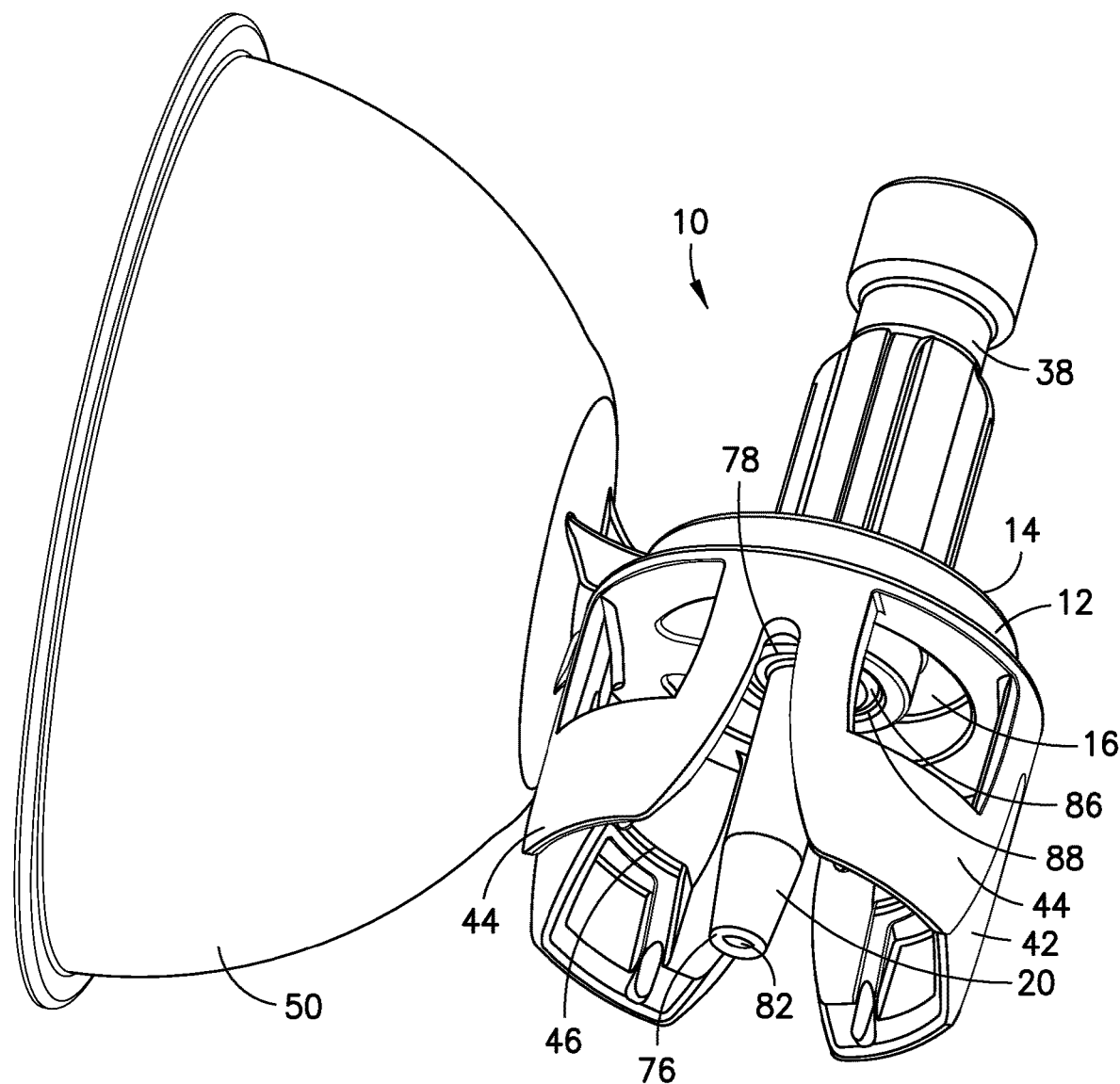
FIG. 1 is a perspective view of a container access device in accordance with the prior art.
Figure 2:
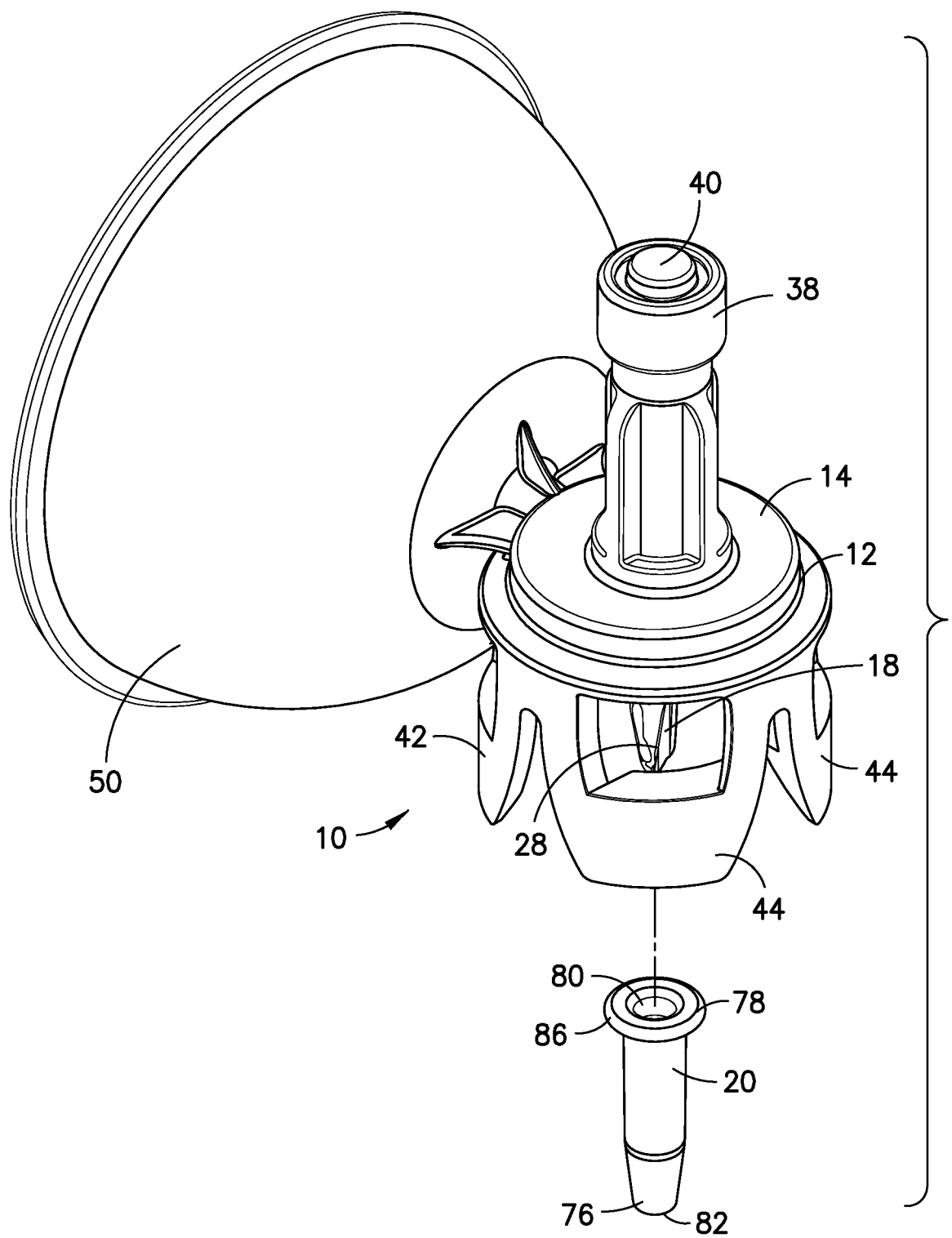
FIG. 2 is an exploded front view of the device of FIG. 1 in accordance with the prior art.
Figure 3:
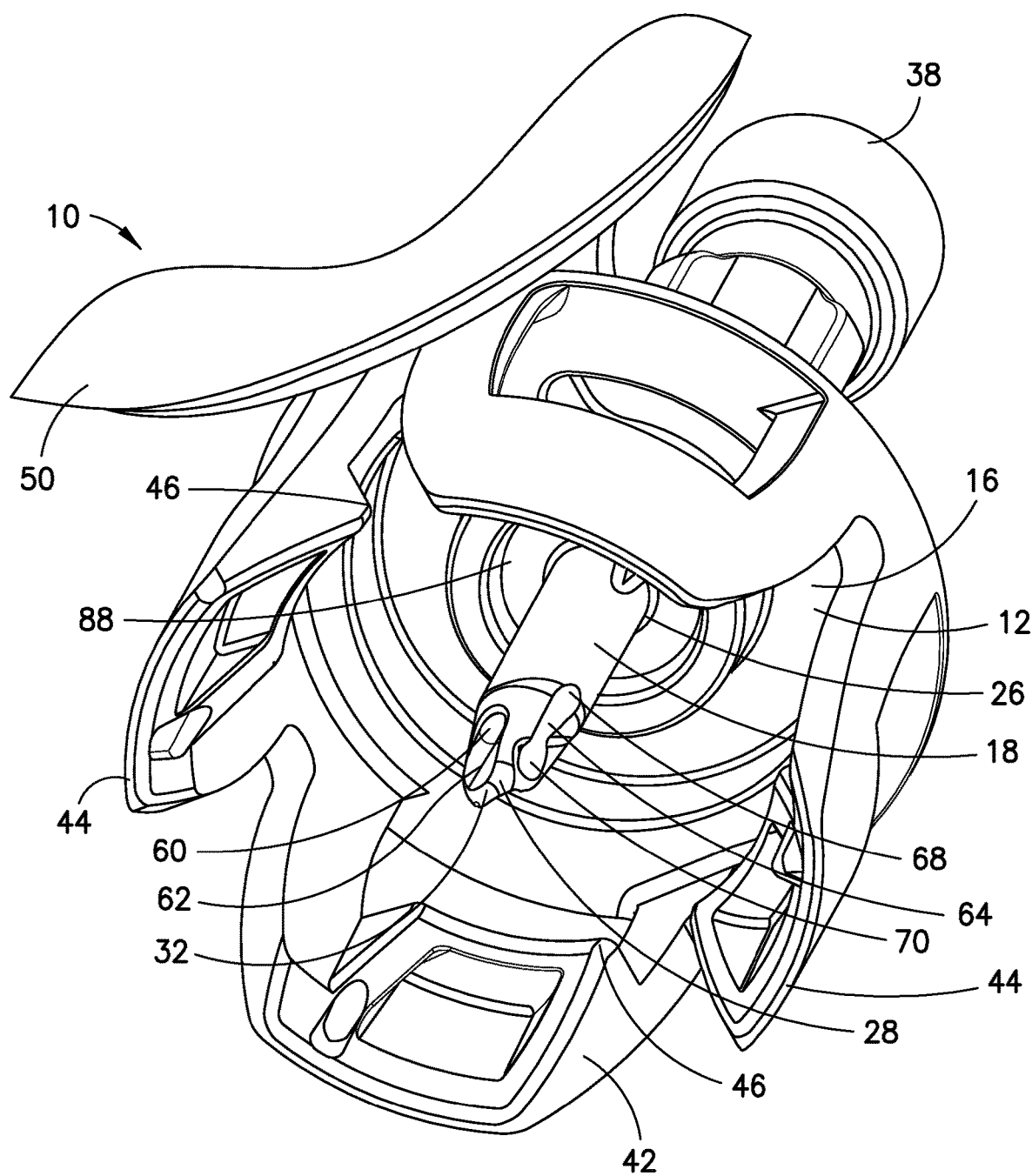
FIG. 3 is a bottom, left-side perspective view of the device of FIG. 1 in accordance with the prior art, showing the device with a sleeve removed.
Figure 4:
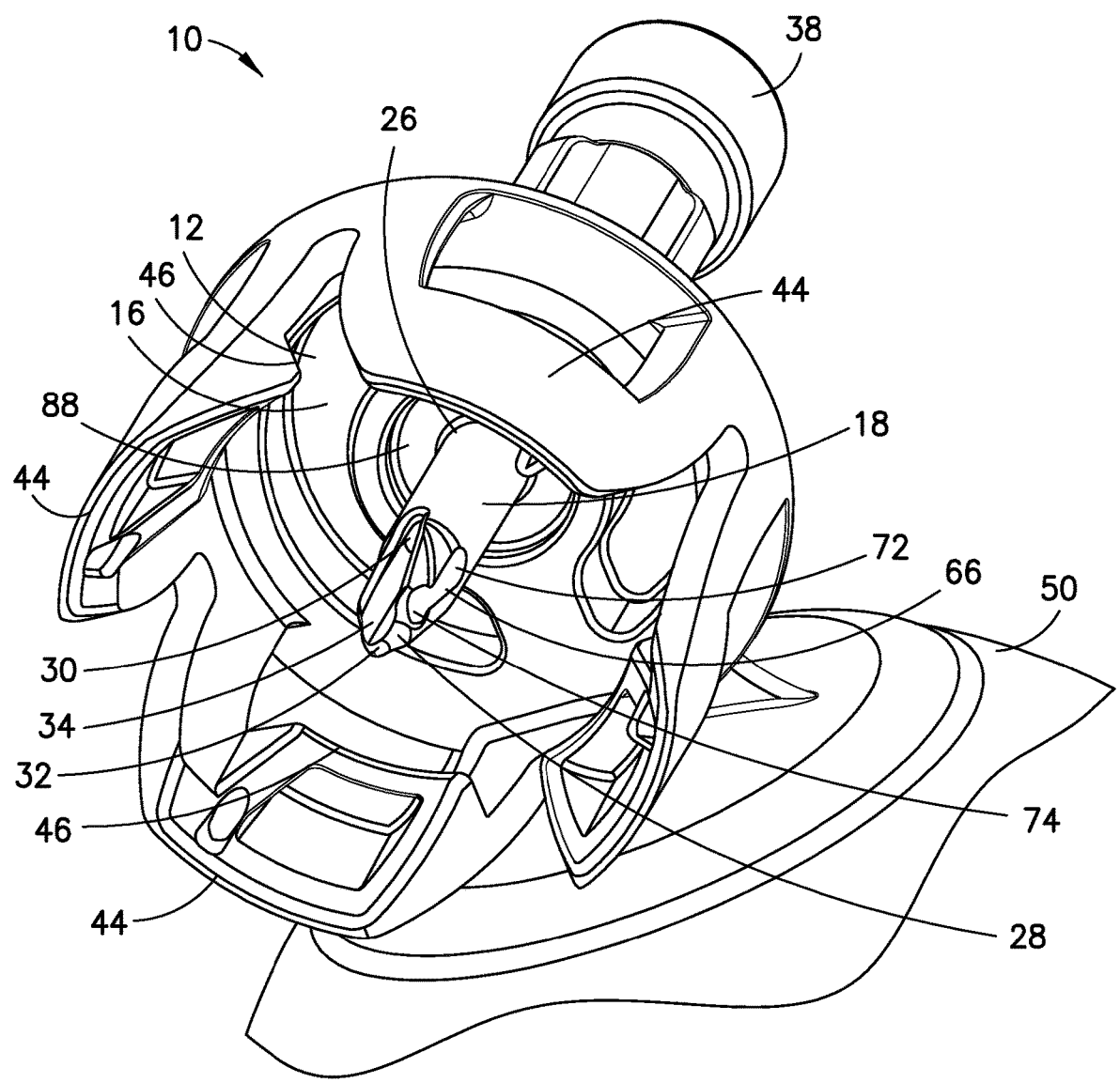
FIG. 4 is a bottom, right-side perspective view of the device of FIG. 1 in accordance with the prior art, showing the device with a sleeve removed.
Figure 5:
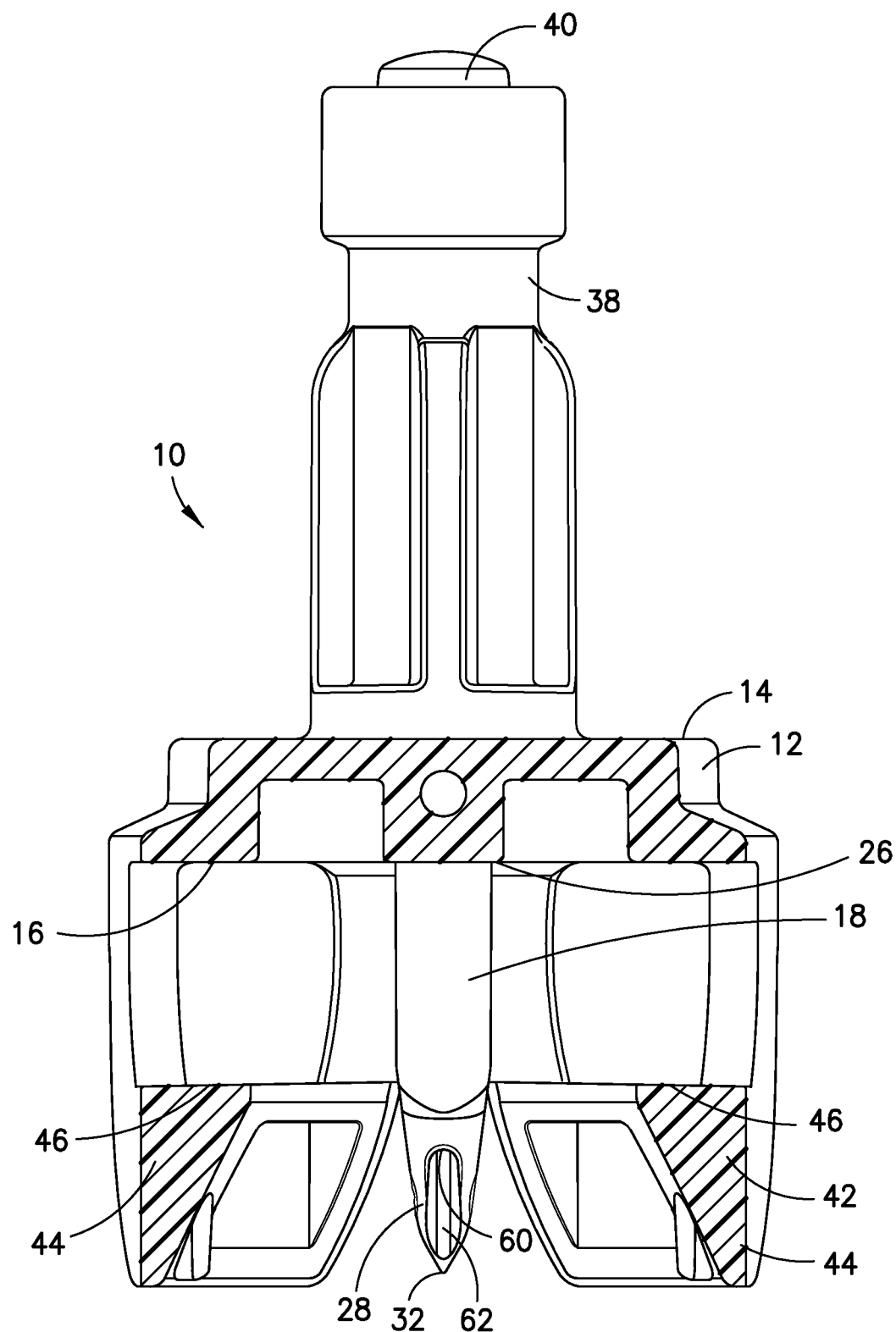
FIG. 5 is a left-side cross-sectional view of the device of FIG. 1 in accordance with the prior art, showing the device with a sleeve removed.

For purposes of the description hereinafter, the terms such as "end", "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting. Further, it is to be understood that the invention may assume various alternative variations and step sequences, except where expressly specified to the contrary.

Figure 9:
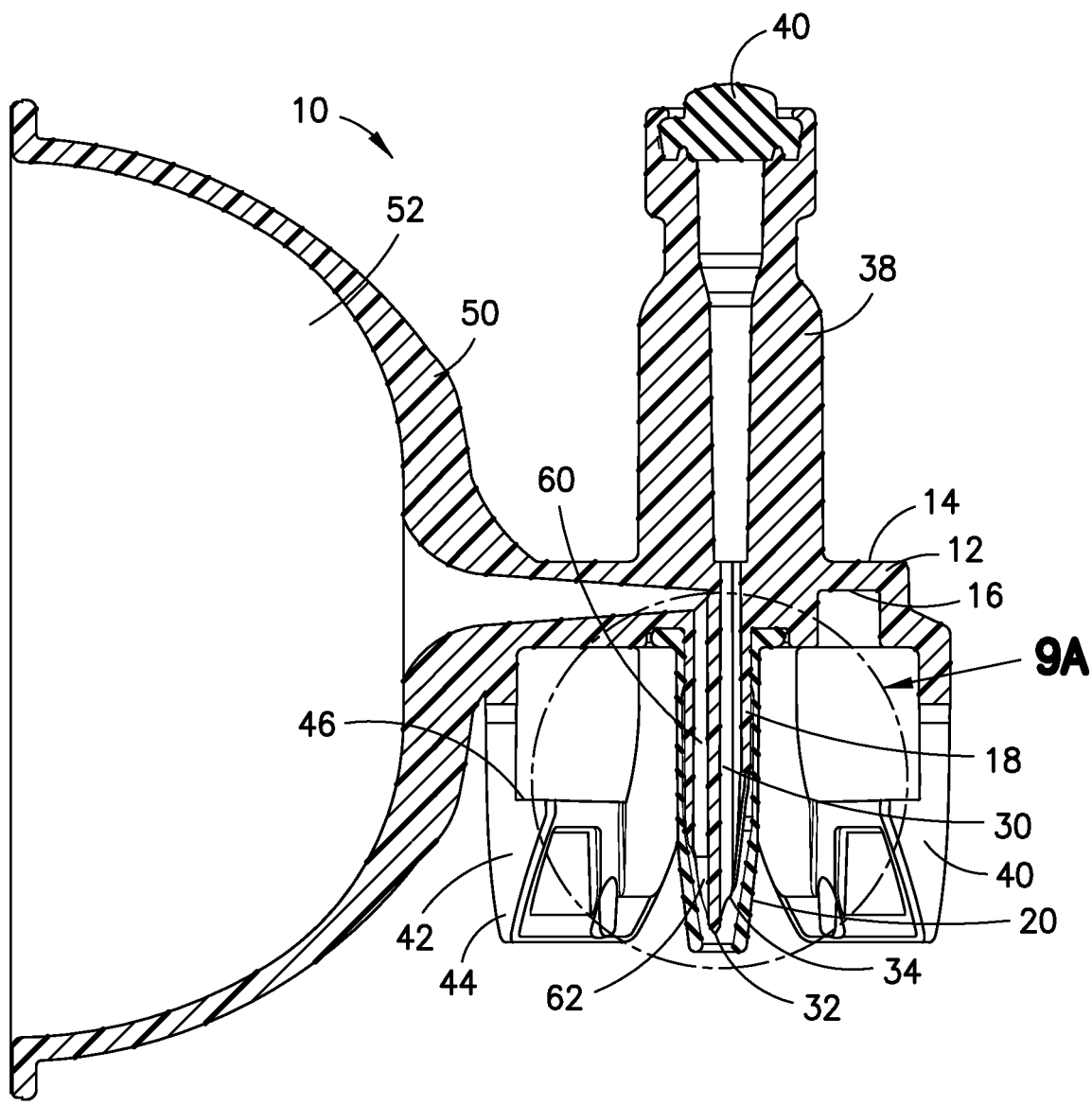
FIG. 9 is a cross-sectional view taken along line 9-9 in FIG. 6 in accordance with the prior art.
Figure 10:
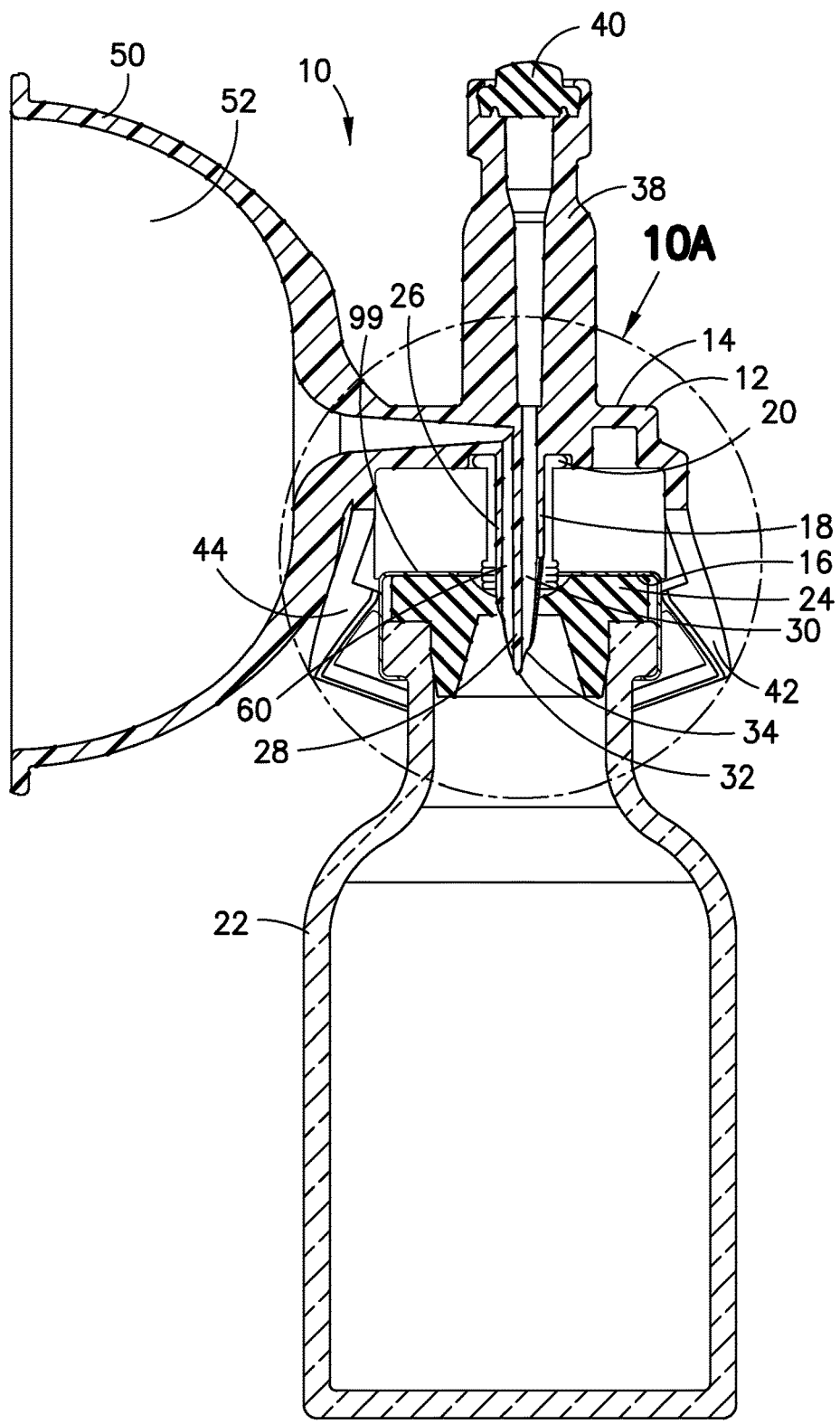
FIG. 10 is a cross-sectional view of the device of FIG. 1 in accordance with the prior art, showing the device in the process of accessing and being attached to a container.

Referring to FIGS. 1-11A, a container access device 10, in accordance with the prior art, includes a body 12 having a first side 14 and a second side 16, a piercing member 18 extending from the second side 16 of the body 12, and a retractable sleeve 20 surrounding the piercing member 18. The container access device 10 is configured to transfer fluid from a fluid container 22 having a sealing member 24, which is shown in FIG. 10. The fluid container 22 may include, but is not limited to, a vial, a bottle, and a bag such as an infusion bag.

Figure 11:
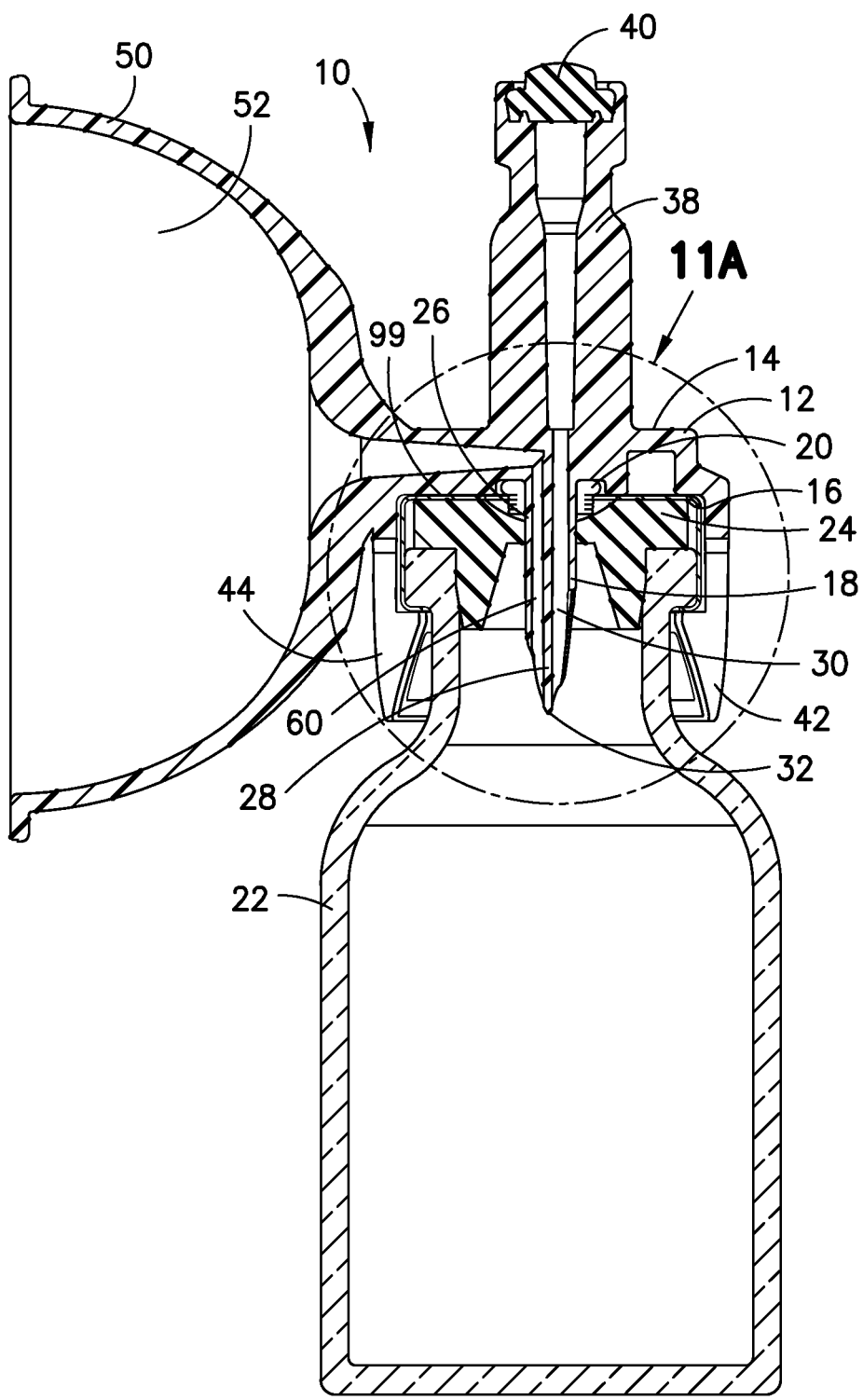
FIG. 11 is a cross-sectional view of the device of FIG. 1 in accordance with the prior art, showing the device accessing a container.

Referring to FIGS. 2-11A, the piercing member 18 has a proximal end 26 and a distal end 28 and defines a longitudinal fluid channel 30. A pointed tip 32 is provided at the distal end 28 for penetrating the sealing member 24 of the container 22. The piercing member 18 has a round cross-section, although other suitable cross-sections may be utilized, including, but not limited to, oval, square, and varying cross-sections. Preferably, the piercing member 18 has a round cross-section to provide a sufficient seal with the sealing member 24 when the device is in use. The piercing member 18 defines a fluid opening 34 in fluid communication with the longitudinal fluid channel 30 that extends from the distal end 28 of the piercing member 18 towards the proximal end 26 of the piercing member 18. The fluid opening 34 can be of any suitable shape, including, but not limited to, rectangular, square, circular, oval, or keyhole. In the embodiments shown in FIGS. 2-11A, the fluid opening 34 is oval-shaped. The fluid opening 34 extends longitudinally along about 50% of the length of the piercing member 18, either from the distal end 28 of the piercing member 18 or a few millimeters from the distal end 28 of the piercing member 18, to ensure that at least part of the fluid opening 34 is located substantially adjacent to an innermost side 36 of the sealing member 24 when the device 10 is in use. The length of the fluid opening 34 can be selected based on the thickness of the thinnest sealing member 24 that it is intended to penetrate, and the distance which the piercing member 18 is intended to penetrate the sealing member 24. As shown in FIG. 11, the sealing member 24 overlaps the fluid opening 34 when the device 11 is fully engaged with the container 22. The maximum width of the fluid opening 34 may be equal to at least 20% of the maximum width of the piercing member 18, and is preferably at least 50% of the maximum width of the piercing member 18. The fluid opening 34 may not necessarily extend in a direction parallel or collinear to the longitudinal axis of the device 10 and may extend in a zig-zag pattern along the length of the piercing member 18 or may be defined by a plurality of openings that extend transversely to the longitudinal axis of the device 10.

Figure 10A:
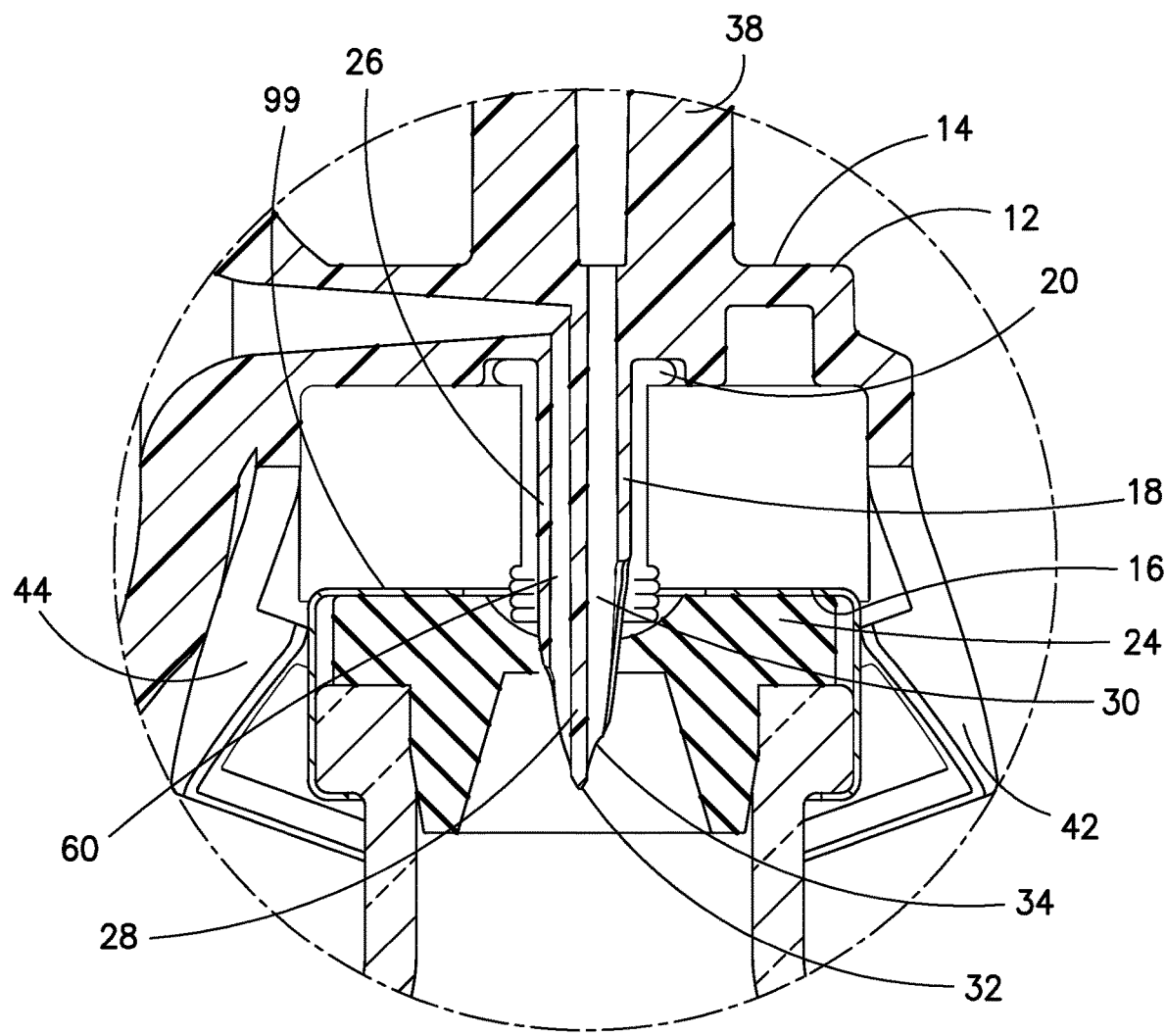
FIG. 10A is an enlarged cross-sectional view of the area indicated in FIG. 10 in accordance with the prior art.
Figure 11A:
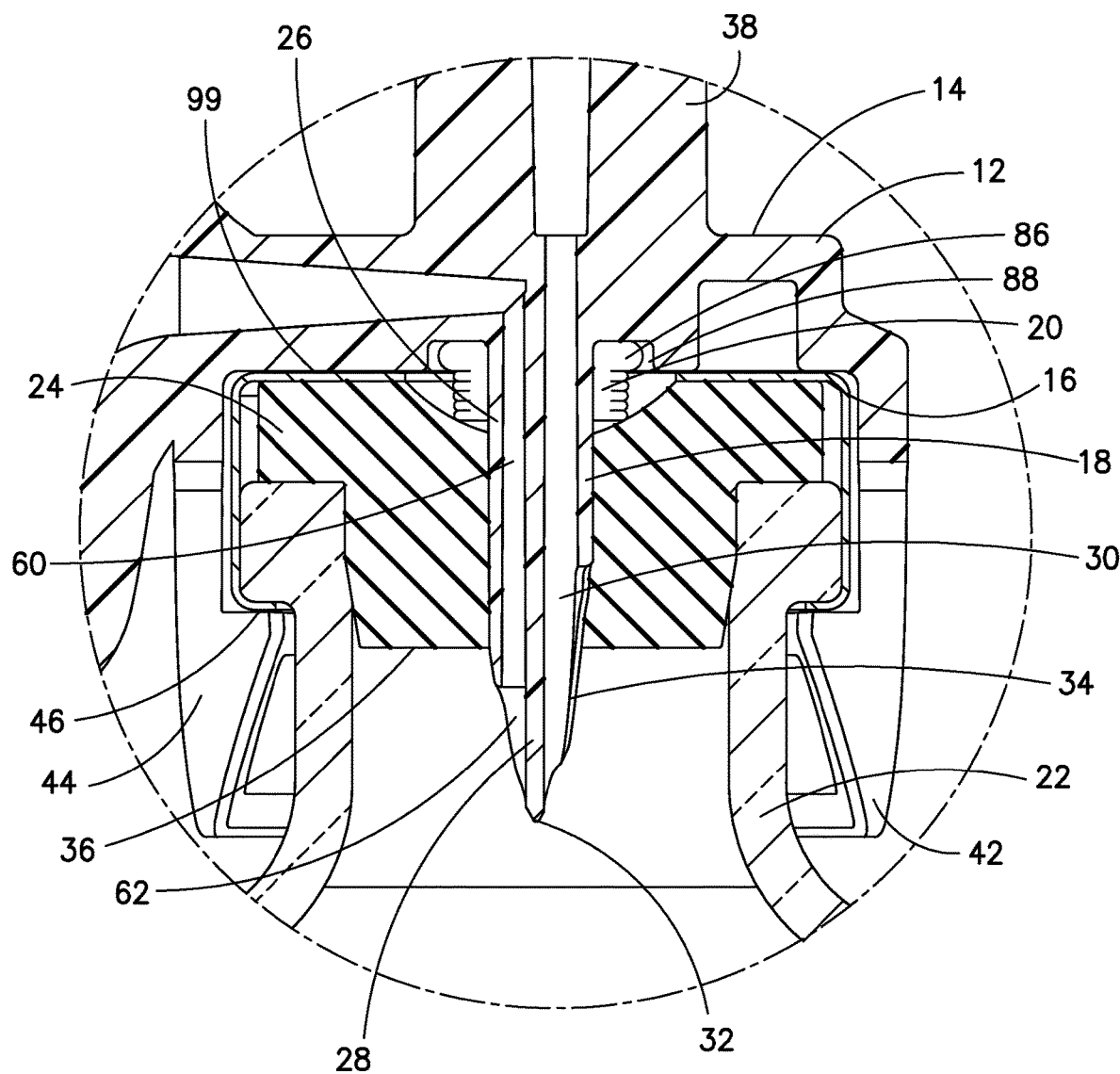
FIG. 11A is an enlarged view of the area indicated in FIG. 11 in accordance with the prior art.

Referring still to FIGS. 2-11A, the body 12 includes a first connecting portion 38 extending from the first side 14 of the body 12. The first connecting portion 38 is configured to attach the device 10 to a syringe adapter or other suitable device or container to allow removal or insertion of fluid into the fluid container 22. As shown in FIG. 9, the first connecting portion 38 is shaped and configured to receive a mating connector, such as a collet arrangement, although other suitable connections may be utilized, including, but not limited to, a luer arrangement, a snap-fit mechanism, a threaded luer lock, and other suitable mechanical or non-mechanical connecting arrangements. The longitudinal fluid channel 30 extends through the body 12 and is in fluid communication with the first connecting portion 38. The first connecting portion 38 may include a septum or membrane 40 to seal the fluid channel 30 at the first connecting portion 38. The body 12 may also include a second connecting portion 42 extending from the second side 16 of the body 12 of the device 10 that is configured to secure the device 10 to the fluid container 22. The second connecting portion 42 includes a plurality of resilient arms 44 having protrusions 46 that engage the rim of the fluid container 22 when the piercing member 18 has been pushed through the sealing member 24 of the fluid container 22, although other suitable arrangements for the second connecting portion 42 may be utilized. As shown in FIGS. 10 and 10A, the resilient arms 44 deflect radially outward when the device 10 is in the process of being attached to the fluid container 22 and return to their original position after being fully secured to the container as shown in FIGS. 11 and 11A.

Figure 6:
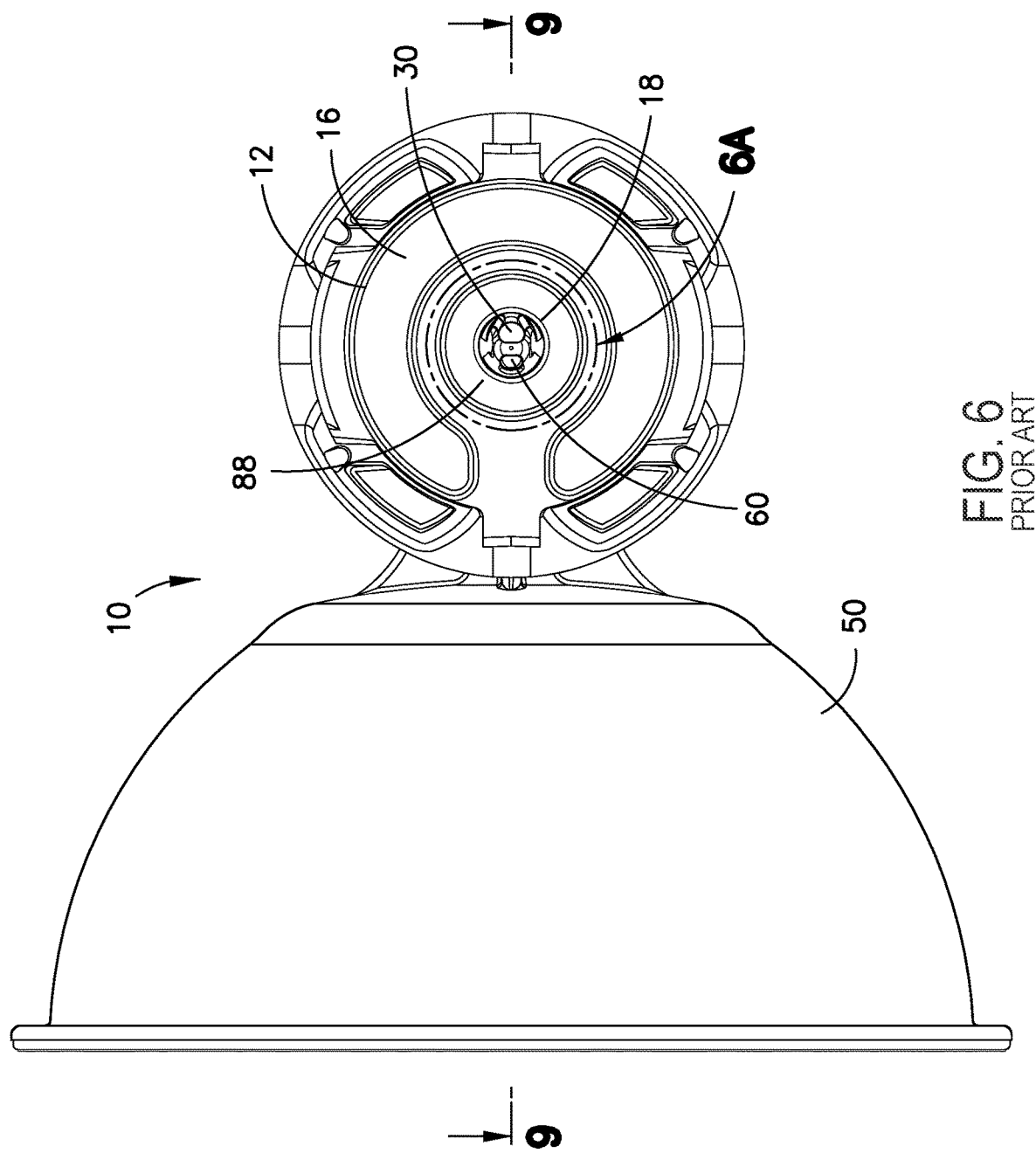
FIG. 6 is a bottom view of the device of FIG. 1 in accordance with the prior art, showing the device with a sleeve removed.
Figure 6A:
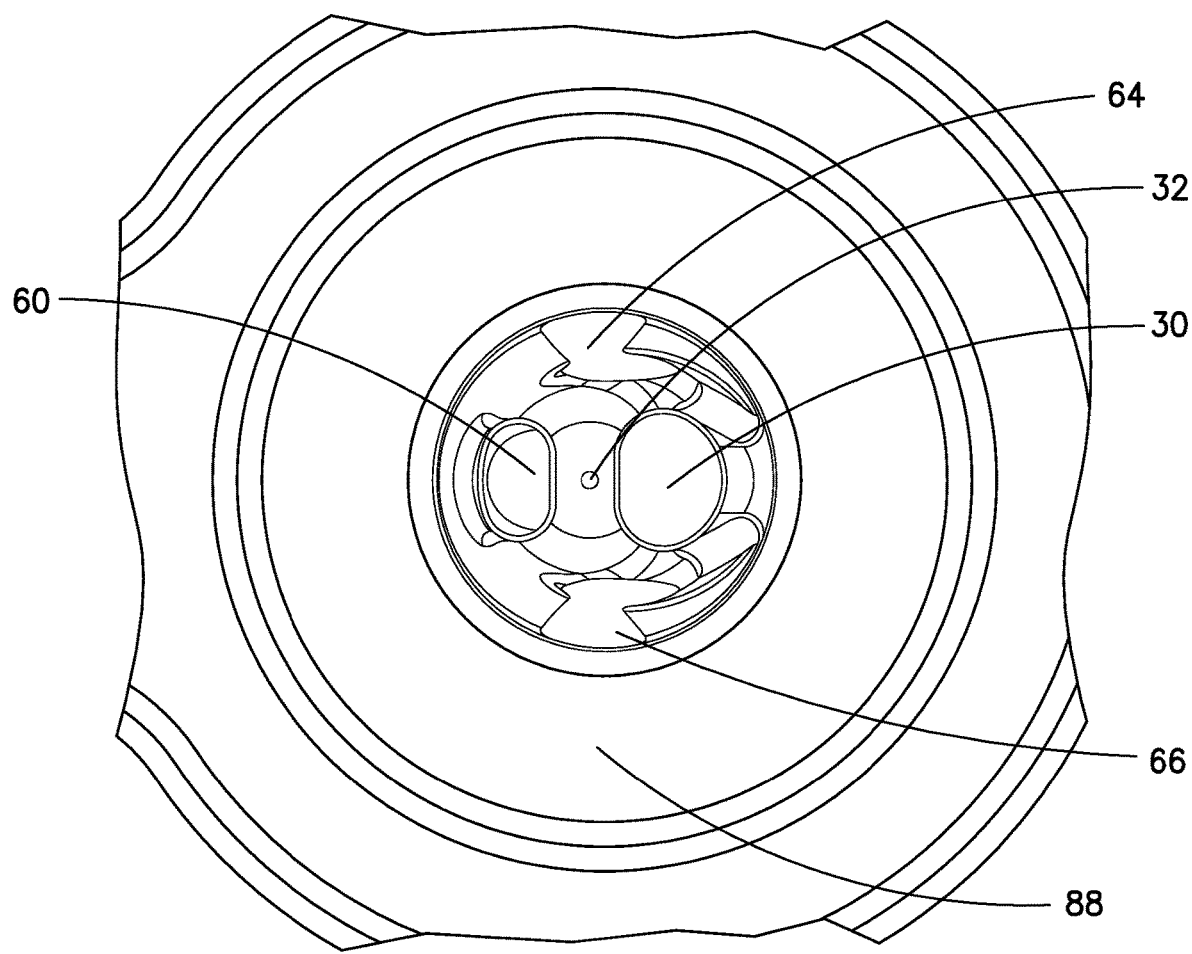
FIG. 6A is an enlarged view of the area indicated in FIG. 6 in accordance with the prior art.
Figure 7:
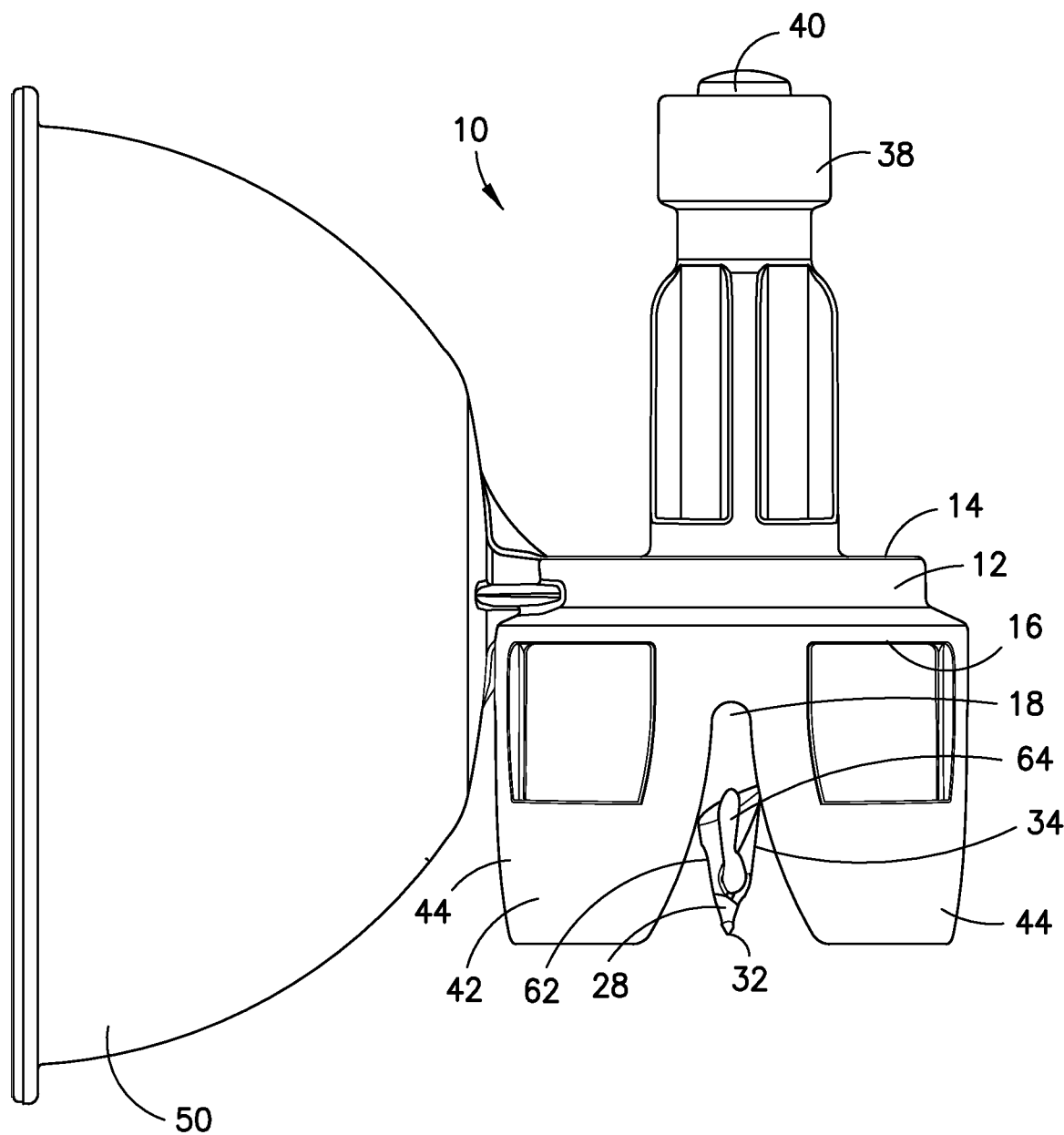
FIG. 7 is a left-side view of the device of FIG. 1 in accordance with the prior art, showing the device with a sleeve removed.
Figure 8:
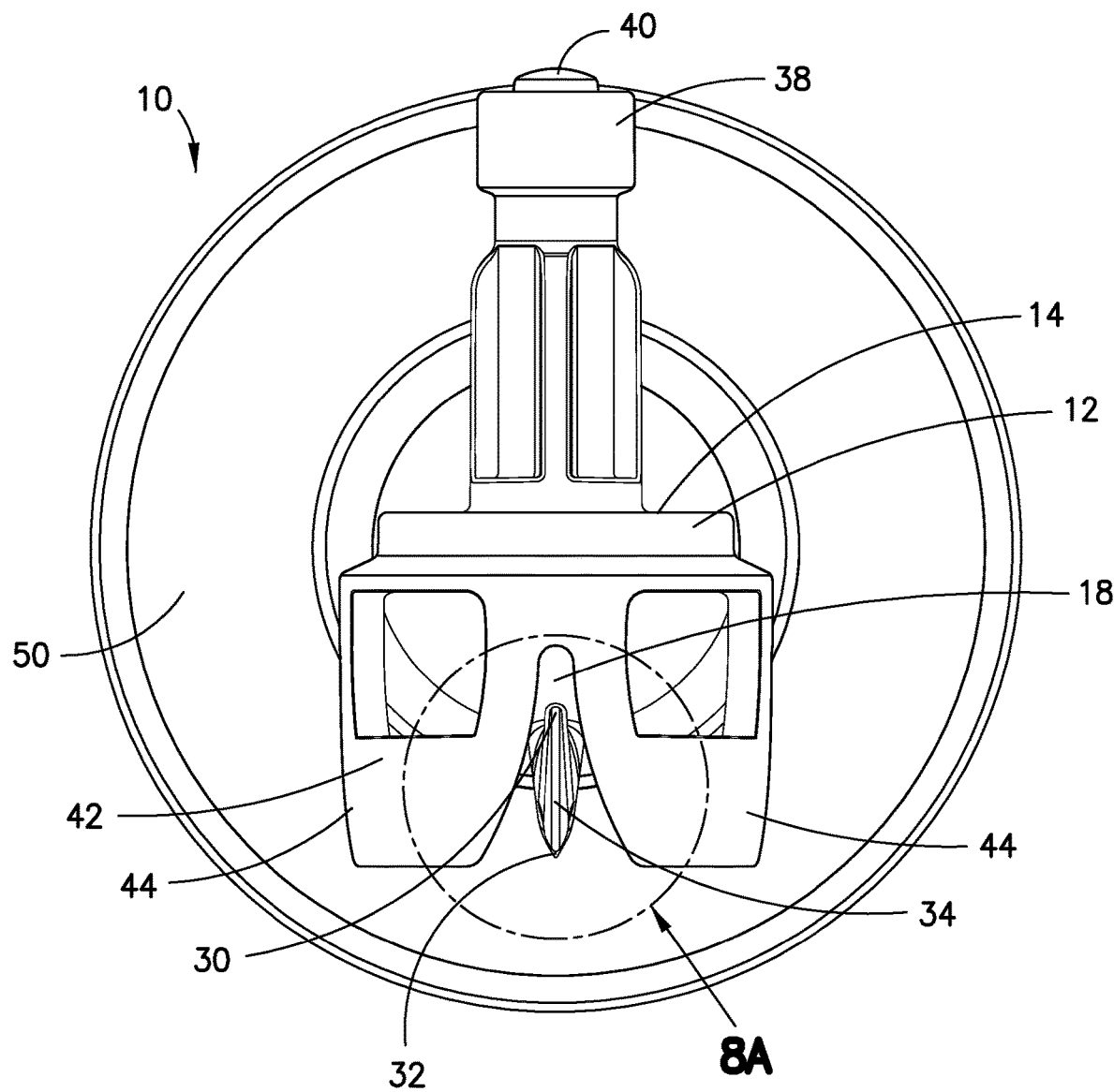
FIG. 8 is a rear view of the device of FIG. 1 in accordance with the prior art, showing the device with a sleeve removed.
Figure 8A:
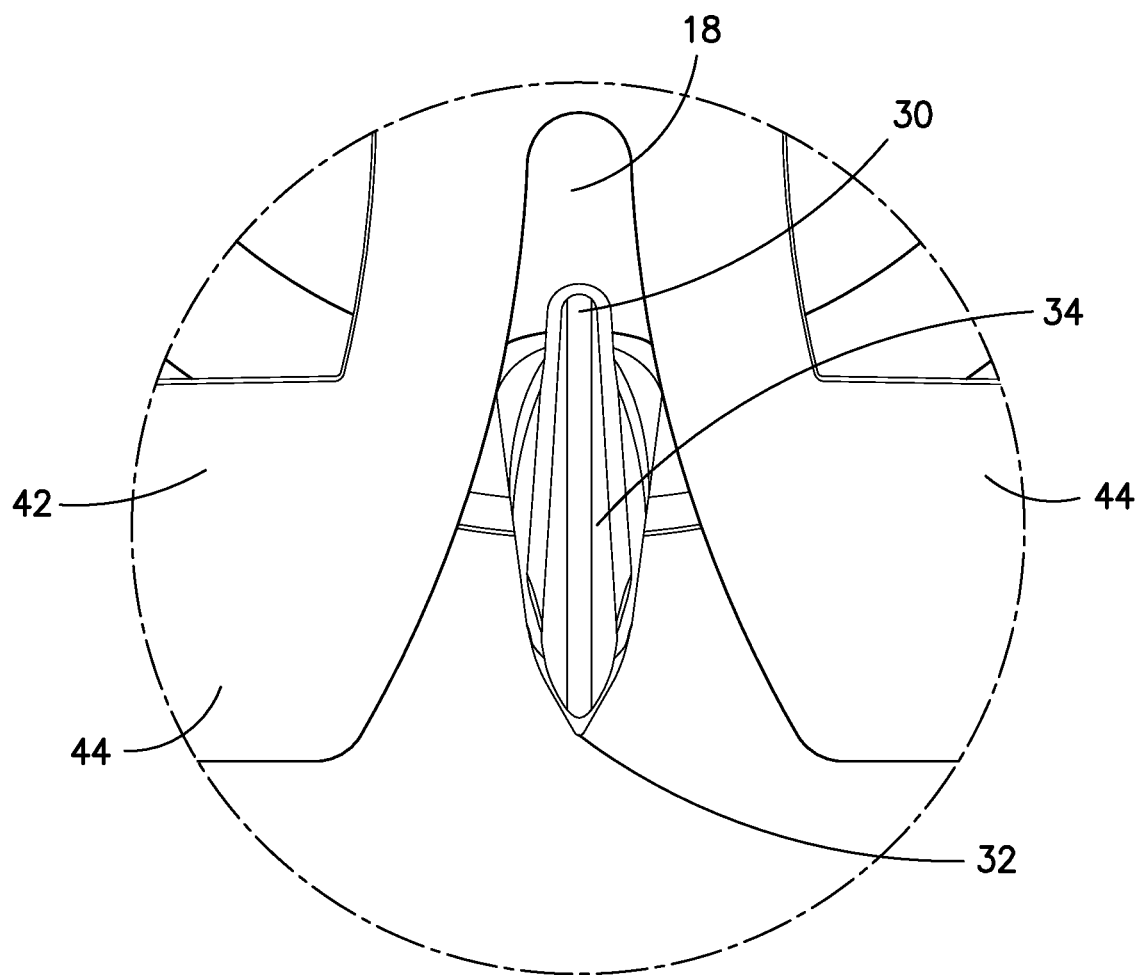
FIG. 8A is an enlarged view of the area indicated in FIG. 8 in accordance with the prior art.

Referring again to FIGS. 2-11A, the device 10 further includes a pressure equalization arrangement 50 that is configured to equalize the pressure within the container 22 during fluid transfer through the use of an expansible chamber 52. The piercing member 18 defines a longitudinal vent channel 60 and a vent opening 62 extending from the distal end 28 of the piercing member 18 or a few millimeters from the distal end 28 of the piercing member 18 toward the proximal end 26 of the piercing member 18. The vent opening 62 is in fluid communication with the longitudinal vent channel 60. The longitudinal vent channel 60 extends through the body 12 of the device 10 and is in fluid communication with the expansible chamber 52 of the pressure equalization arrangement 50. In particular, during use of the device 10, the longitudinal vent channel 60 and the pressure equalization arrangement 50 is utilized to regulate the pressure within the fluid container 22 and contains the medicament and any vapor thereof within the device 10 and within the fluid container 22. The pressure equalization arrangement 50 may be the balloon or membrane arrangement shown in U.S. Pat. No. 8,523,838, which is hereby incorporated by reference in its entirety, although other suitable pressure equalization arrangements may be utilized, such as, but not limited to, a filtered vent exit. Further, although not shown, the pressure equalization arrangement may include a filter, such as a hydrophobic filter, positioned between the chamber 52 and the longitudinal vent channel 60. The longitudinal fluid channel 30 and longitudinal vent channel 60 may have any suitable cross-section including, but not limited to, round, oval, elliptical, semi-circular, and square. As shown more clearly in FIG. 6A, the cross-sections of the longitudinal fluid channel 30 and longitudinal vent channel 60 are elliptical or semi-circular, so that their cross-sectional areas can be maximized within the cylindrical piercing member 18.

Referring to FIGS. 2-8A, the piercing member 18 includes first and second flat portions 64, 66 positioned circumferentially between the vent opening 62 and the fluid opening 34 with the first flat portion 64 positioned opposite the second flat portion 66. The first and second flat portions 64, 66 each include a first end 68, 72 and a second end 70, 74. The first and second ends 68, 70, 72, 74 of the flat portions 64, 66 are generally bulbous-shaped with a tapered middle that is narrower than the first and second ends 68, 70, 72, 74. The first and second flat portions 64, 66 are generally planar. The first and second flat portions 64, 66 are configured to reduce the force needed for the piercing member 18 to penetrate the sealing member 24 of the fluid container 22.

Referring to FIGS. 1, 2, 9, and 9A, the retractable sleeve 20 has a distal end 76 and a proximal end 78 and surrounds the piercing member 18. The retractable sleeve 20 may be made from an elastomeric material including, but not limited to, thermoplastic or thermosetting elastomers including, but limited to, silicone rubber. The retractable sleeve 20 has a proximal opening 80 that surrounds the proximal end 26 of the piercing member 18 and a distal opening 82 that is positioned beyond the distal end 28 of the piercing member 18 in the longitudinal direction. Thus, there is a space between the distal opening 82 of the sleeve 20 and the distal end 28 of the piercing member 18. An inner surface of the retractable sleeve 20 has a shape approximating the shape of the outer surface of the piercing member 18. A gap 84 is defined between the inner surface of the retractable sleeve 20 and the outer surface of the piercing member 18. The gap 84 may have a substantially uniform width, i.e., the distance between the inner surface of the retractable sleeve 20 and the outer surface of the piercing member 18 is substantially uniform. The distal opening 82 of the retractable sleeve 20 is in fluid communication with the gap 84, so that sterilizing gases or liquids, such as ETO gas, can enter the gap 84 to sterilize both the inner surface of the retractable sleeve 20 and the outer surface of the piercing member 18. A seal is present between the proximal end 78 of the retractable sleeve 20 and the proximal end 26 of the piercing member 18. The mating surfaces of the seal between the proximal end 78 of the retractable sleeve 20 and the proximal end 26 of the piercing member 18 are never exposed to the atmosphere even during use of the device 10.

Figure 9A:
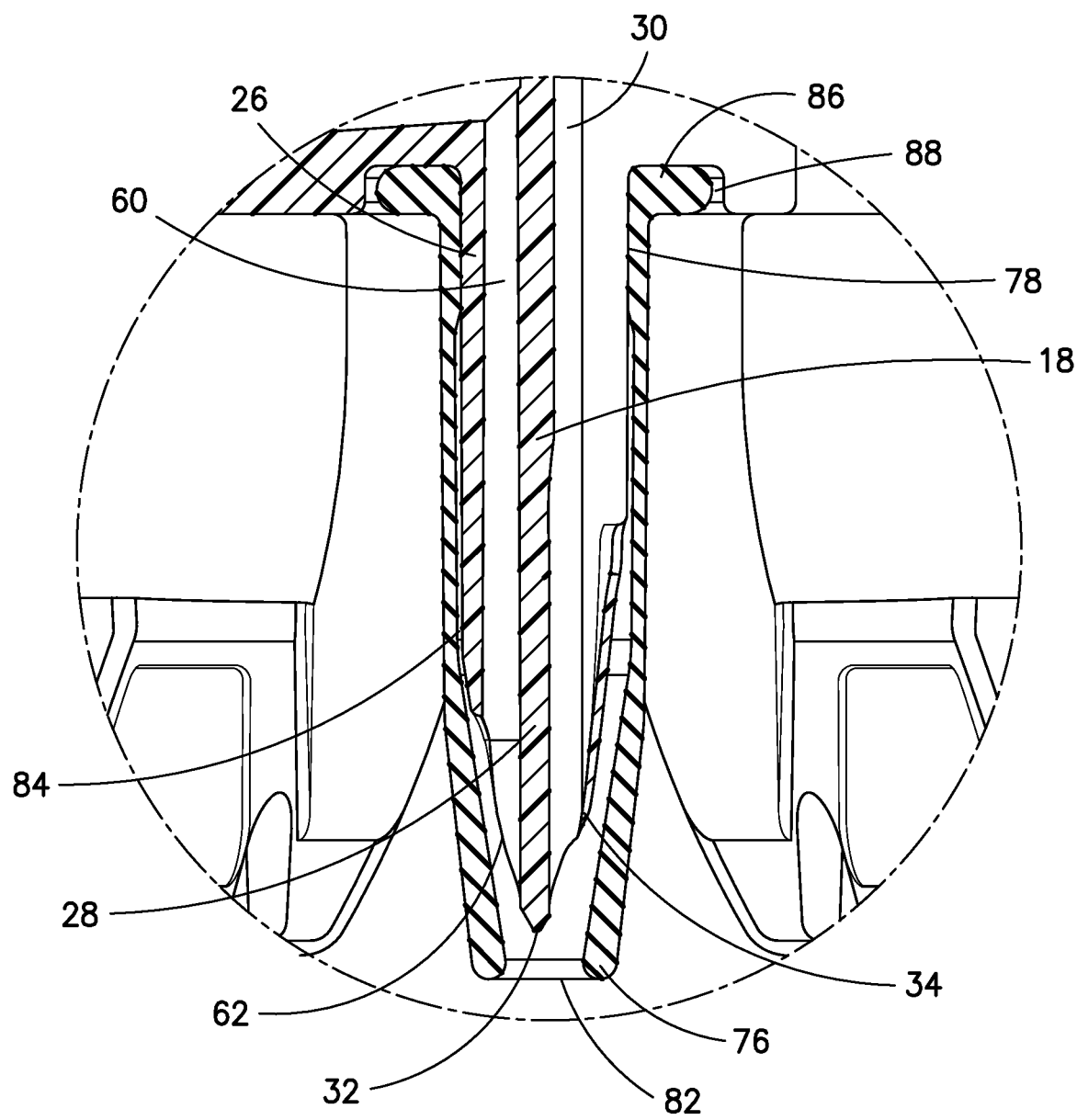
FIG. 9A is an enlarged view of the area indicated in FIG. 9 in accordance with the prior art.

Referring to FIGS. 9 and 9A, the seal between the retractable sleeve 20 and the piercing member 18 may be formed by an interference fit between the proximal end 78 of the retractable sleeve 20 and the proximal end 26 of the piercing member 18. The interference fit may be accomplished by increasing the cross-sectional thickness of the retractable sleeve 20 at its proximal end 78. The retractable sleeve 20 may also be provided with a lip 86 at the proximal end 78. This lip 86 is configured to abut the second side 16 of the body 12 and may be accommodated by an annular groove 88 defined by the body 12 of the device 10. The lip 86 allows the retractable sleeve 20 to be easily assembled over the piercing member 18 by placing the retractable sleeve 20 into a rigid tubular tool, such that an end of the tool abuts the lip 86. The tool can then be used to push the retractable sleeve 20 onto the piercing member 18.

Figure 12:
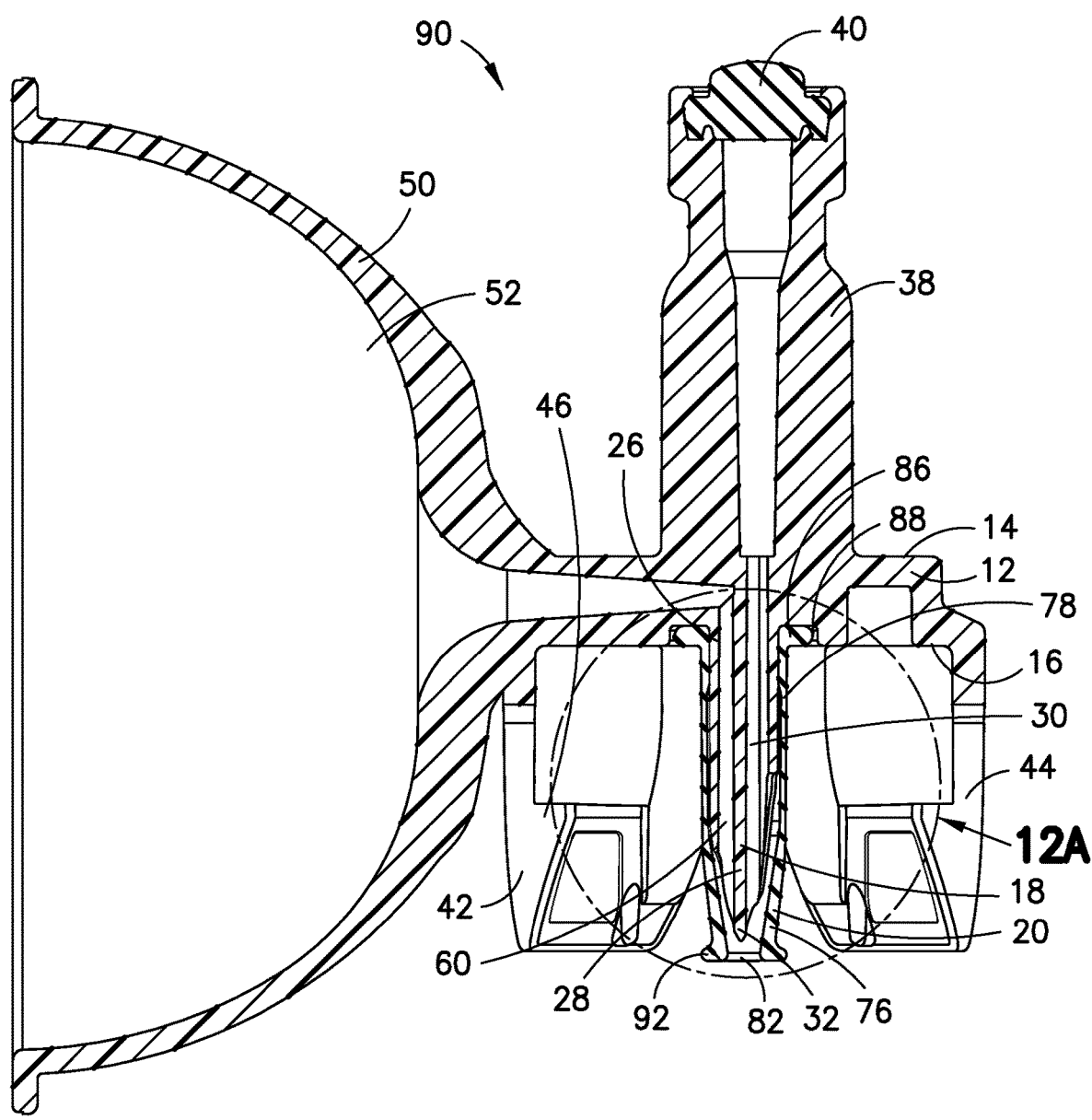
FIG. 12 is a cross-sectional view of a container access device in accordance with a second embodiment of the prior art.
Figure 12A:
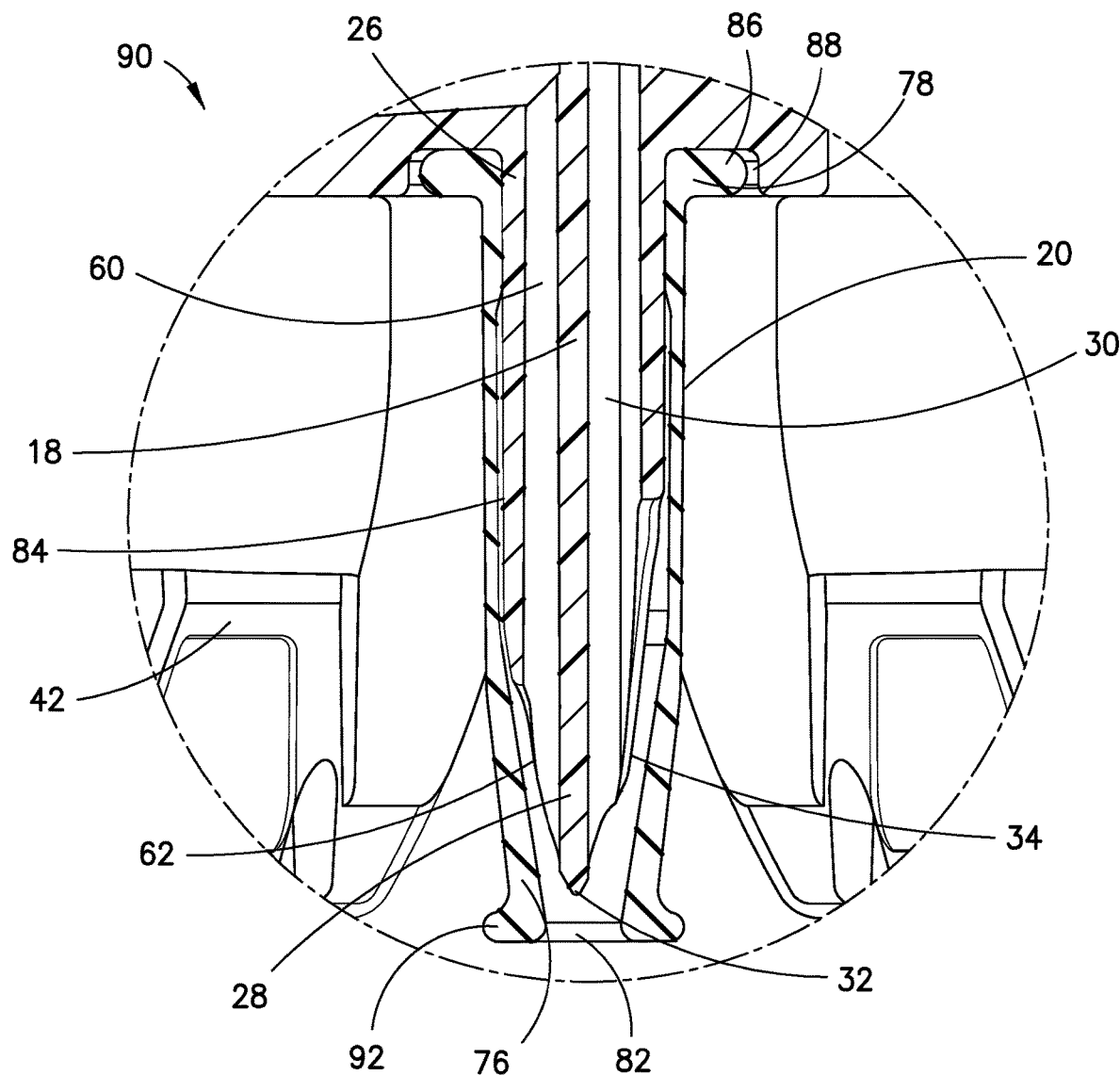
FIG. 12A is an enlarged view of the area indicated in FIG. 12 in accordance with the prior art.

Referring to FIGS. 12 and 12A, a further embodiment of a container access device 90 is shown. The access device 90 is similar to the device 10 shown in FIGS. 1-11A and like reference numbers are used for like elements. The access device 90 shown in FIG. 12, however, includes a lip 86 adjacent the distal opening 82 in order to provide a better seal with the sealing member 24 of the fluid container 22 when the device 10 is in use.

Figure 13:
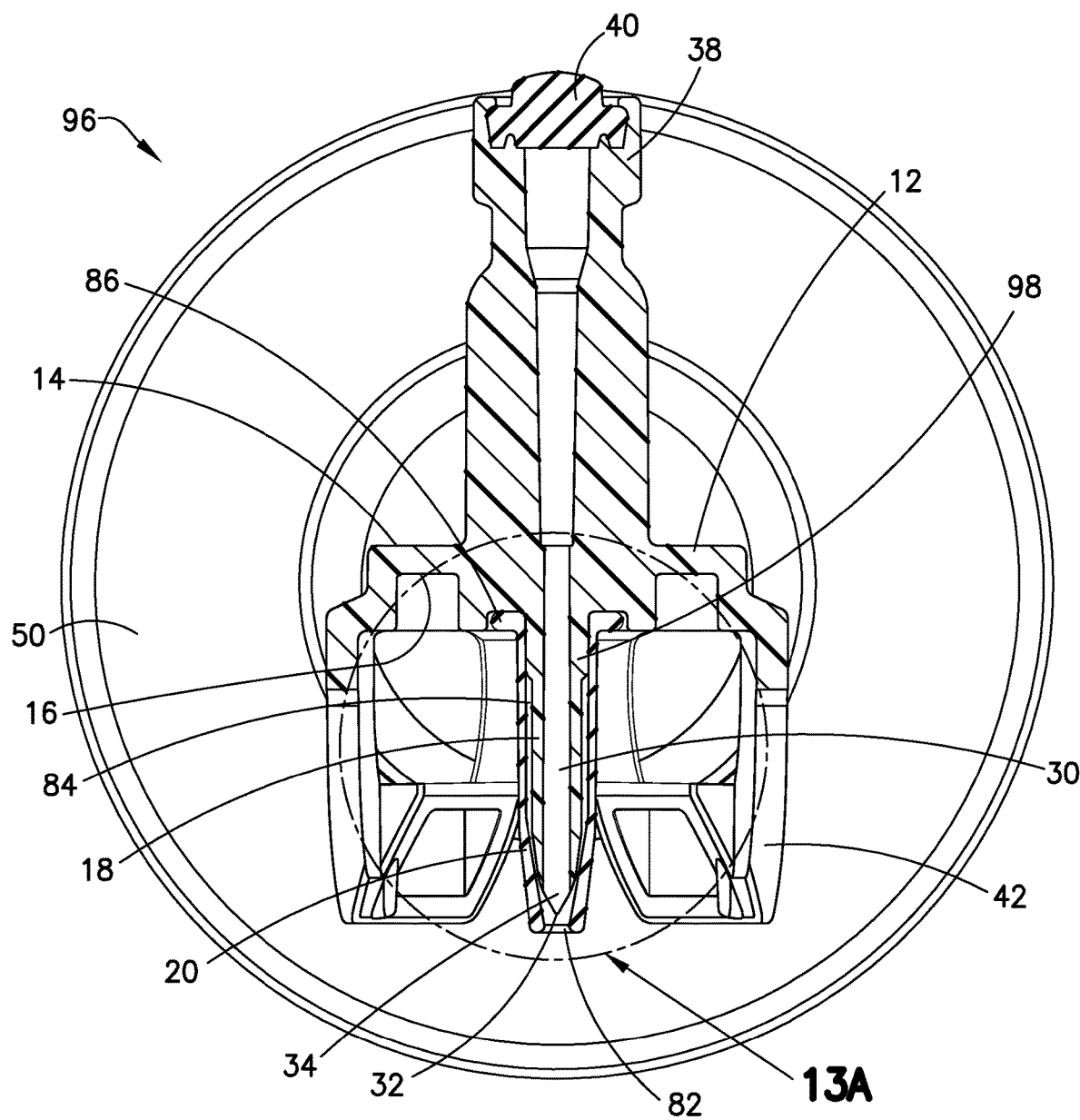
FIG. 13 is a cross-sectional view of a container access device in accordance with a third embodiment of the prior art.
Figure 13A:
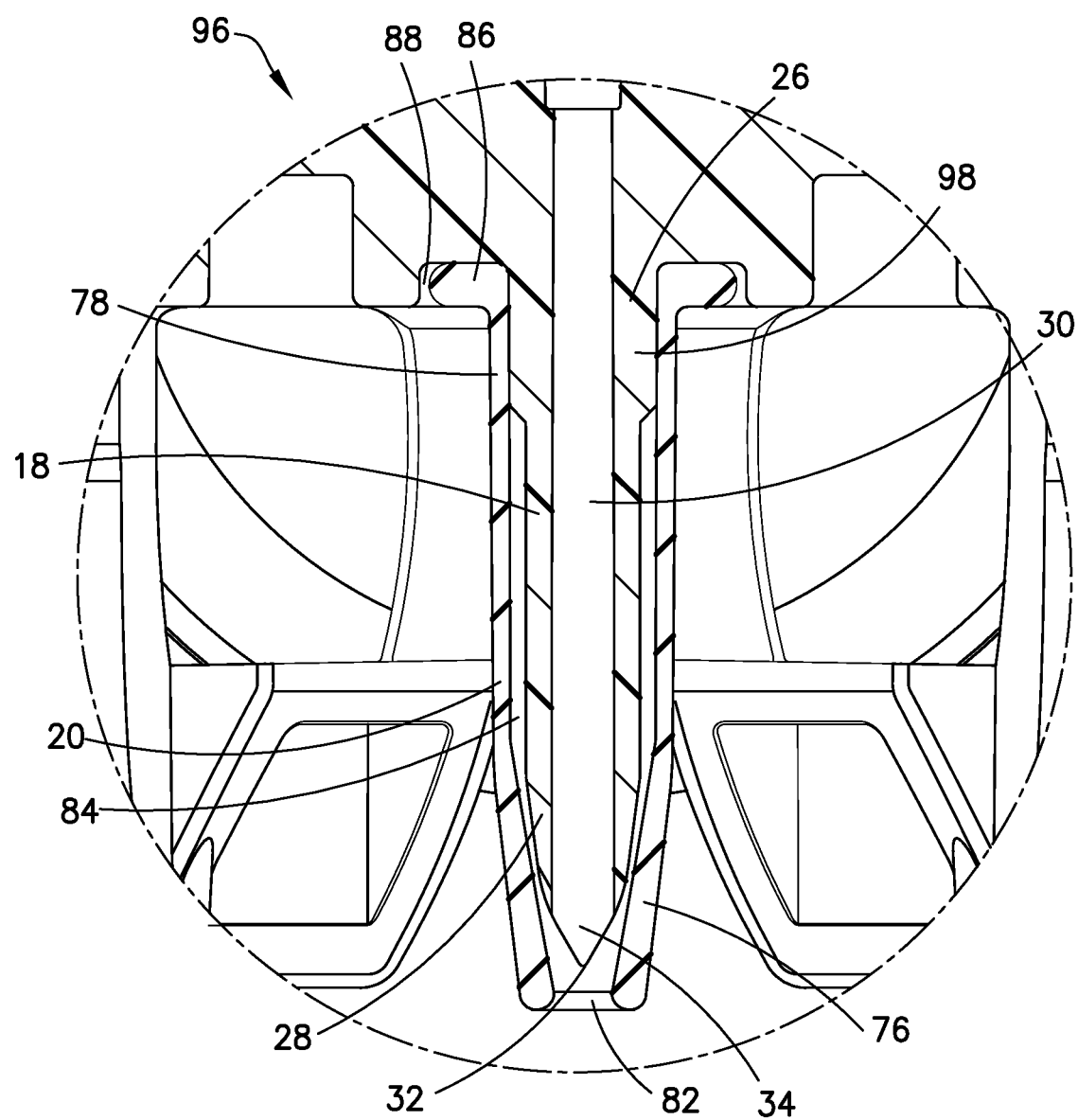
FIG. 13A is an enlarged view of the area indicated in FIG. 13 in accordance with the prior art.

Referring to FIGS. 13 and 13A, another embodiment of a container access device 96 is shown. The access device 96 is similar to the device 10 shown in FIGS. 1-11A and like reference numbers are used for like elements. The access device 96 in FIG. 13, however, obtains an interference fit between the retractable sleeve 20 and the piercing member 18 by increasing the thickness of a portion 98 of the piercing member 18 at its proximal end 26. Also, as shown in FIG. 13, the access device 96 may only have a longitudinal fluid channel 30 and no vent opening.

Referring again to FIGS. 1, 2, and 9-11A, the retractable sleeve 20 is configured to abut against an outermost side 99 of the sealing member 24 when the device 10 has been inserted into a fluid container 22 and to retract as the piercing member 18 penetrates more deeply into the sealing member 24. When the device 10 is fully inserted into the sealing member 24 of the fluid container 22, as shown in FIG. 11, at least a portion of the fluid opening 34 is exposed to the interior of the fluid container 22, while the remaining portion of the fluid opening 34 is sealed by the sealing member 24 of the fluid container 22, thereby preventing deterioration or contamination of the contents of the fluid container 22 and preventing the contents of the fluid container 22 from leaking out and contaminating the surrounding environment. More specifically, as shown in FIGS. 10 and 10A, as the piercing member 18 is entering the fluid container 22, the fluid opening 34 spans the thickness of the sealing member 24 of the fluid container 22. Without the retractable sleeve 20, toxic vapors or substances could potentially be expelled to the surrounding atmosphere or contaminants could potentially enter into the fluid container 22. The retractable sleeve 20 provides a seal with the sealing member 24 of the fluid container 22 and retracts as the piercing member 18 is inserted into the fluid container 22 to prevent any leakage into or out of the fluid container 22. Further, the elongated size and shape of the fluid opening 34 allows the fluid container 22 to be completely emptied when the fluid container 22 is inverted, which is typical during the withdrawal of medicament from the fluid container 22. If the entirety of the fluid opening 34 were positioned within the fluid container 22, all of the medicament may not be emptied from the fluid container 22 depending on the size of the sealing member 24.

As the piercing member 18 is inserted through the sealing member 24 and into the fluid container 22, the retractable sleeve 20 is compressed between the sealing member 24 and body 12 of the device 10, as shown in FIGS. 10-11A. This forms a seal between the retractable sleeve 20 and the sealing member 24 and between the retractable sleeve 20 and the body 12 of the device 10, thereby assuring that none of the contents of the fluid container 22 is exposed to the atmosphere during transfer of the fluid.

The length of the piercing member 18, the fluid opening 34, and the retractable sleeve 20 may be selected, such that several conditions are met when the device 10 is inserted into the sealing member 24 of the fluid container 22. First, a portion of the fluid opening 34 is disposed within the fluid container 22 to allow fluid to flow into or out of the fluid container 22 via the longitudinal fluid channel 30 in the piercing member 18. Second, the retractable sleeve 20 is compressed, such that the distal end 76 of the retractable sleeve 20 forms a seal with the sealing member 24 and the proximal end 78 of the retractable sleeve 20 forms a seal with the body 12 of the device 10.

Further, the configuration of the device 10 allows for the last drop of fluid to be withdrawn from a variety of the fluid containers 22 having different configurations and different thickness sealing members 24. At the same time, the configuration of the retractable sleeve 20 assures that access to the fluid container 22 and transfer of the fluid occurs in a sealed manner, so that no fluids or gases escape from or enter the system while still allowing the entire system to be sterilized. In particular, the gap 84 between the retractable sleeve 20 and the piercing member 18 allows the piercing member 18 and the inner surface of the retractable sleeve 20 to be sterilized. The retractable sleeve 20 also prevents contact contamination of the piercing member 18 before it is inserted into the fluid container 22.

Reference is now made to FIGS. 14-16B, which show a piercing member, generally indicated as 118, for use with a fluid transfer device, generally indicated as 110, in accordance with the invention. The piercing member 118 has a distal end 128 and a proximal end 126 and defines a longitudinal fluid channel 130. The piercing member 118 can have a round cross-section, however, it can be appreciated that the piercing member can have other cross-sections, including but not limited to, oval, square, and varying cross-sections. A first opening 134 is positioned at the distal end 128 of the piercing member 118. The first opening 134 is in fluid communication with the longitudinal fluid channel 130. A cover or "flash" 135 is positioned over the first opening 134. The cover 135 includes a pre-cut pattern 136, so that the cover 135 opens along the pre-cut pattern 136 upon application of a distally directed force from the longitudinal fluid channel. In accordance with the invention, a "flash" is defined as a covering that closes the fluid orifice or first opening 134 of the piercing member 118 in a molded configuration.

Figure 16:
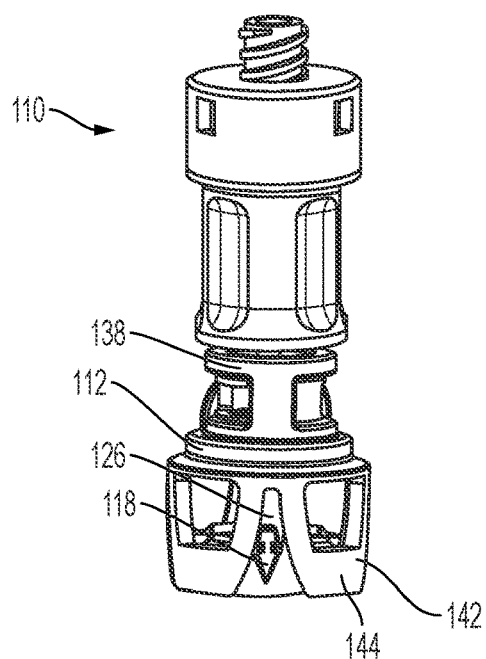
FIG. 16 is a side perspective view of a portion of a fluid transfer device of FIG. 14 wherein the covering/flash is open in accordance with an embodiment of the present invention.
Figure 16A:
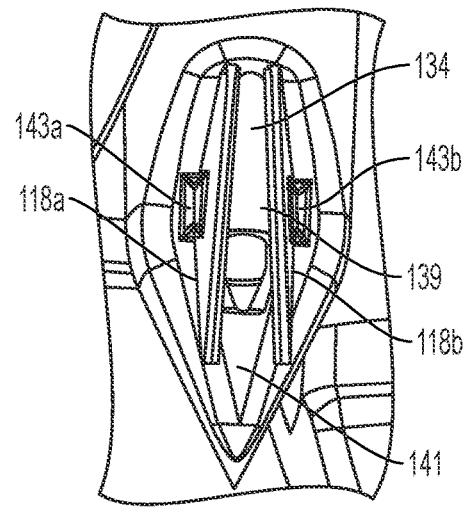
FIG. 16A in an enlarged front perspective view of the spike of FIG. 16 in accordance with an embodiment of the present invention.
Figure 16B:
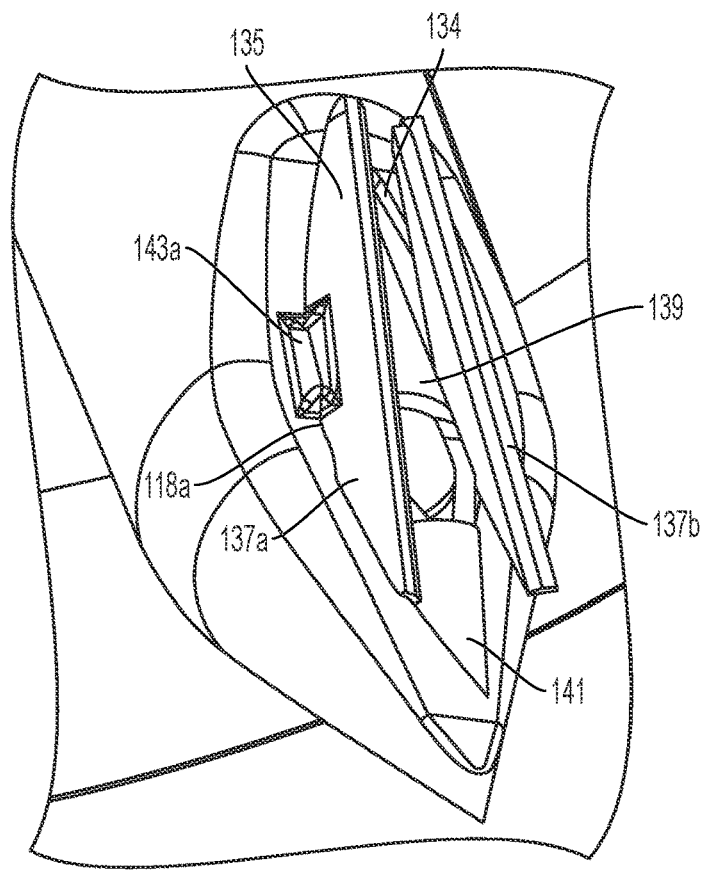
FIG. 16B is an enlarged side perspective view of the spike of FIG. 16 in accordance with an embodiment of the present invention.

This distally directed force can be applied via a cannula 139, as shown in FIGS. 16, 16A, and 16B, extending through the fluid channel 130 having a distal tip 141, which comes into contact with the cover 135 and applies a force to the cover 135 causing the cover to break along the pre-cut pattern 136.

According to one embodiment, the cover 135 can be a membrane that is molded over the first opening 134. The cover 135 can include at least one molded hinge 143 connecting the cover 135 to the piercing member 118. According to a further embodiment, the pre-cut pattern 136 can include a cut along a center portion 137 of the cover dividing the cover into a first cover portion 137a and a second cover portion 137b and the at least one molded hinge 143 can comprise a first hinge 143a for securing the first cover portion 137a to a first portion 118a of the piercing member 118 and a second hinge 143b for securing the second cover portion 137b to a second portion 118b of the piercing member 118. The second hinge 143b securing the second cover portion 137b to the second portion 118b of the piercing member 118 is at a location that is opposite from the first hinge 143a securing the first cover portion 137a of the first portion 118a of the piercing member 118. During use of the device 110, application of the distally directed force causes the cover 135 to open along the first and second hinges 143a, 143b in an outward direction with respect to the first opening 134, as shown in FIGS. 16-16B.

According to one embodiment, the at least one molded hinge 143 and/or the first and second hinges 143a, 143b can be living hinges and the cover 135 remains attached to the piercing member 118 via the at least one molded hinge 143 and/or the first and second hinges 143a, 143b.

Figure 15:
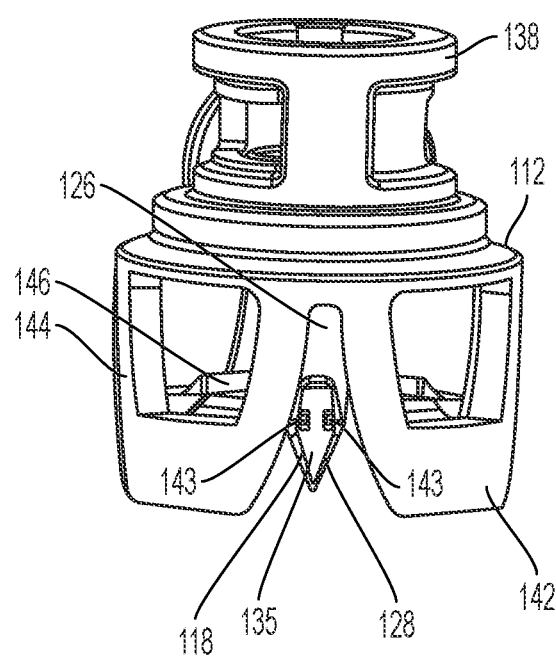
FIG. 15 is a side perspective view of a portion of the fluid transfer device of FIG. 14 wherein the covering/flash is closed in accordance with an embodiment of the present invention.
Figure 15A:
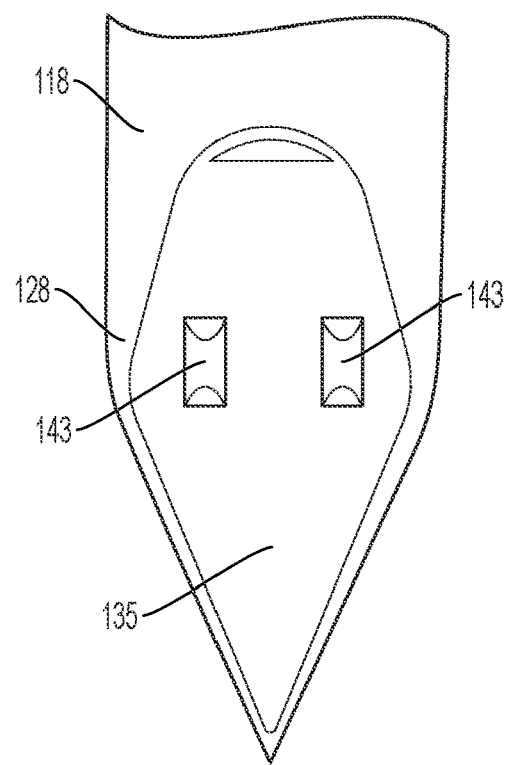
FIG. 15A is an enlarged front view of the spike and flash of FIG. 15 in accordance with an embodiment of the present invention.
Figure 15B:
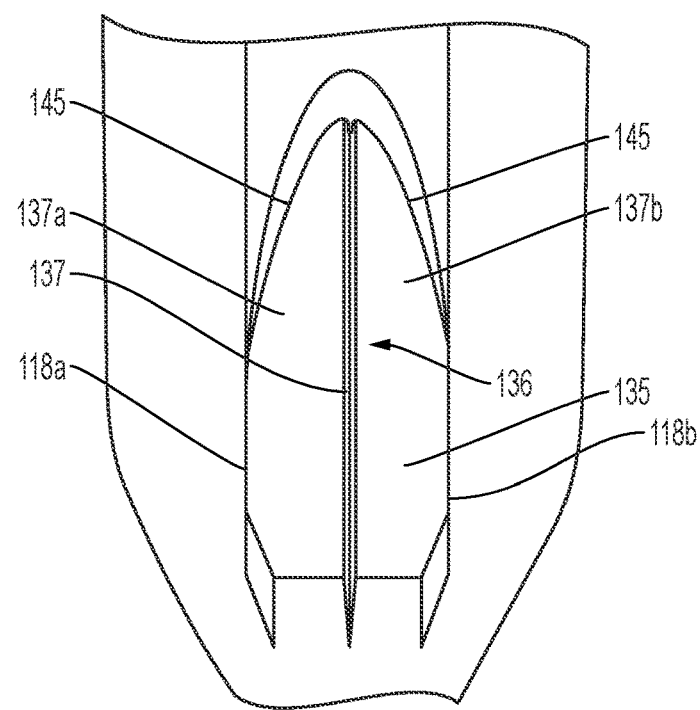
FIG. 15B is a partial front view of the covering/flash of FIG. 15A showing the cutting pattern of the pre-cut pattern of the covering/flash in accordance with an embodiment of the present invention.

With reference to FIG. 15B, the pre-cut pattern can include cuts 145 that partially surround the first opening 134, with the exception of the first and second portions 118a, 118b, so that during use, the cover 135 remains attached to the piercing member 118 via the first and second hinges 143a, 143b.

Figure 14:
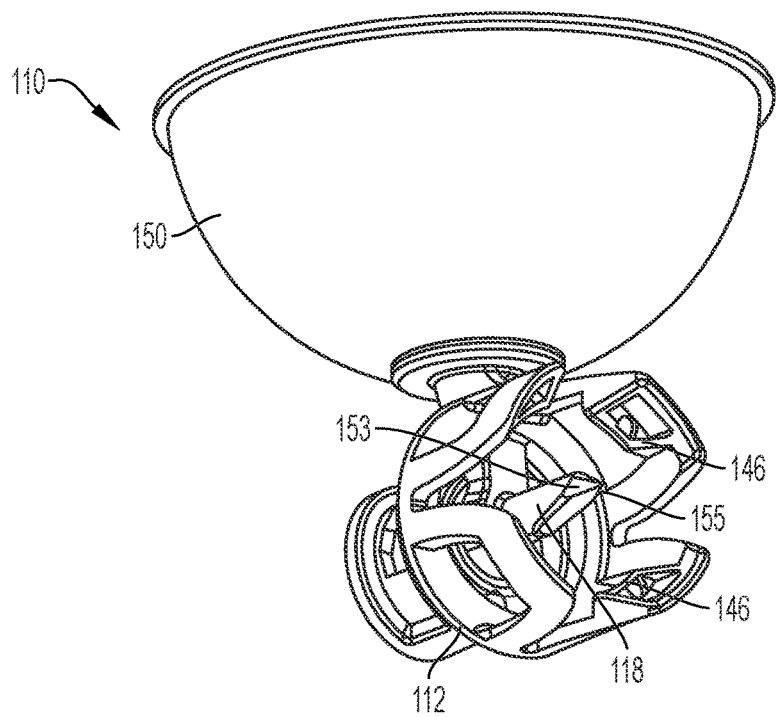
FIG. 14 is a perspective view of a portion of a fluid transfer device including the piercing member in accordance with an embodiment of the present invention.
Figure 14A:
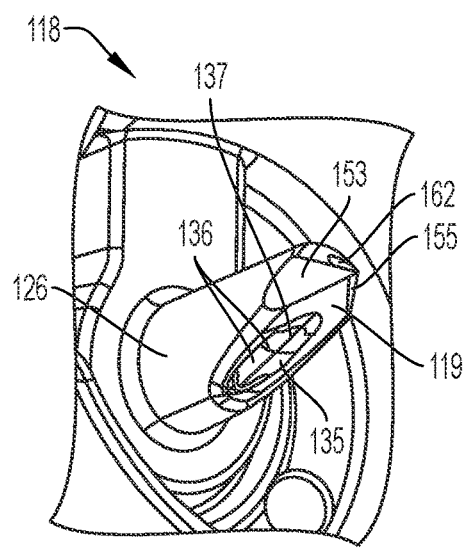
FIG. 14A in an enlarged perspective view of the spike of FIG. 14 in accordance with an embodiment of the present invention.
Figure 14B:
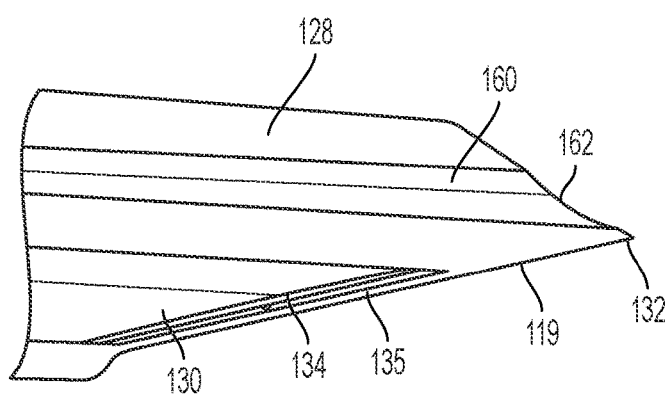
FIG. 14B is a side view of the spike of FIG. 14A in accordance with an embodiment of the present invention.

The distal end 128 of the piercing member 118, at the location of the first opening 134 can include a steep taper 119, such as shown in FIGS. 14A and 14B. The steep taper 119 forms a slanted orifice for the first opening 134 which facilitates last drop withdrawal from a container, such as container 22 shown in FIG. 10. As shown in FIG. 10, the container 22 has a sealing member 24. Providing a steep taper 119 on the piercing member 118 of the invention enables the piercing member 118 to be used with sealing members 24 having varying thicknesses and/or sizes.

With continuing reference to FIGS. 14A and 14B, the piercing member 118 defines a longitudinal vent channel 160 and defines a second opening 162 at the distal end 128 of the piercing member 118. With further reference to FIGS. 14 and 15, the fluid transfer device 110 further comprises a body 112 extending from the proximal end 126 of the piercing member 118. This body 112 can include a first connecting portion 138 configured for receiving a mating connector, such as a collet arrangement, although other suitable connections may be utilized, including, but not limited to, a luer arrangement, a snap-fit mechanism, a threaded luer lock, and other suitable mechanical or non-mechanical connecting arrangements. A second connecting portion 142 is configured to secure the body 112 to a container. The second connecting portion 142 can include a plurality of resilient arms 144 having protrusions 146 that engage the rim of the fluid container when the piercing member 118 has been pushed through the sealing member of the fluid container, although other suitable arrangements for the second connecting portion 142 may be utilized. The resilient arms 144 are designed to deflect radially outward when the device 110 is in the process of being attached to the fluid container and return to their original position after being fully secured to the container.

The device further includes a pressure equalization arrangement 150 in fluid communication with the longitudinal vent channel 160 of the piercing member 118. The pressure equalization arrangement 150 is configured to equalize the pressure within the container during fluid transfer through the use of an expansible chamber, as shown as 52 in FIG. 9. As further shown in FIG. 14B and discussed above, the piercing member 118 defines a longitudinal vent channel 160 and a vent opening or second opening 162 extending from the distal end 128 of the piercing member 118 or a few millimeters from the distal end 128 of the piercing member 118 toward the proximal end 126 of the piercing member 118. The vent opening or second opening 162 is in fluid communication with the longitudinal vent channel 160. The longitudinal vent channel 160 extends through the body 112 of the device 110 and is in fluid communication with the expansible chamber of the pressure equalization arrangement 150. In particular, during use of the device 110, the longitudinal vent channel 160 and the pressure equalization arrangement 150 is utilized to regulate the pressure within the fluid container and contains the medicament and any vapor thereof within the device 110 and within the fluid container. The pressure equalization arrangement 150 may be the balloon or membrane arrangement shown in U.S. Pat. Nos. 8,523,838 or 9,919,826, which are hereby incorporated by reference in their entirety, although other suitable pressure equalization arrangements may be utilized, such as, but not limited to, a filtered vent exit. Further, although not shown, the pressure equalization arrangement may include a filter, such as a hydrophobic filter, positioned between the chamber and the longitudinal vent channel 160. The longitudinal fluid channel 130 and longitudinal vent channel 160 may have any suitable cross-section including, but not limited to, round, oval, elliptical, semi-circular, and square.

The first opening 134 of the piercing member 118 extends longitudinally from the distal end 128 of the piercing member 118. A length of the first opening 134 of the piercing member 118 in a direction extending from the proximal end 126 of the piercing member 118 to the distal end 128 of the piercing member 118 ensures that at least a portion of the first opening 134 of the piercing member 118 is located adjacent an innermost side of a sealing member of a fluid container, when the piercing member 118 has penetrated the sealing member, such as shown for illustration purposes in FIGS. 10-11A, which shows sealing member 24 of fluid container 22 wherein the fluid opening 34 is adjacent the innermost side of the sealing member 24.

According to one embodiment, the piercing member 118 can have a cylindrical shape with a pointed tip 132 at the distal end 128. According to a further embodiment and with reference to FIGS. 14 and 14A, the piercing member 118 can comprise a first flat portion 153 defining a first planar surface and a second flat portion 155 defining a second planar surface, wherein the first and second flat portions 153, 155 are configured to reduce a penetration force required to pierce a sealing member of a fluid container relative to a piercing member not having the first and second flat portions.

Although not shown in FIGS. 14-16B, it can be appreciated that the fluid transfer device 110 of the invention can include the retractable sleeve 20 of the prior art as shown in FIGS. 1, 12, and 13 of the present disclosure.

While certain exemplary embodiments of the present invention have been shown and described herein with reference to certain preferred embodiments thereof, it will be understood by those skilled in the art that various changes in form and details may be made therein without departing from the spirit and scope of the invention.

The invention claimed is:

1. A device for transferring fluids comprising:
a piercing member having a distal end and a proximal end and defining a longitudinal fluid channel, a first opening positioned at the distal end of the piercing member, the opening in fluid communication with the longitudinal fluid channel;
a cover positioned over the first opening, the cover including a pre-cut pattern wherein the cover opens along the pre-cut pattern upon application of a distally directed force from the longitudinal fluid channel; and
a cannula extending through the fluid channel for coming into contact with the cover and applying the distally directed force.

2. A device for transferring fluids comprising:
a piercing member having a distal end and a proximal end and defining a longitudinal fluid channel, a first opening positioned at the distal end of the piercing member, the opening in fluid communication with the longitudinal fluid channel; and
a cover positioned over the first opening, the cover including a pre-cut pattern wherein the cover opens along the pre-cut pattern upon application of a distally directed force from the longitudinal fluid channel, wherein the cover comprises a membrane that is molded over the first opening.

3. The device of claim 1, wherein the cover includes at least one connecting piece connecting the cover to the piercing member.

4. The device of claim 3, wherein the cover remains attached to the piercing member via the at least one connecting piece.

5. The device of claim 3, wherein the pre-cut pattern comprises a cut along a center portion of the cover dividing the cover into a first portion and a second portion and wherein the cover includes at least a first connecting piece for securing the first cover portion to a first portion of the piercing member and a second connecting piece for securing the second cover portion to a second portion of the piercing member at a location opposite from the first portion of the piercing member.

6. The device of claim 5, wherein the cover opens along the first and second connecting pieces in an outward direction with respect to the first opening.

7. The device of claim 5, wherein the pre-cut pattern comprises a cut that partially surrounds the opening, with the exception of the first and second portions, so that the cover remains attached to the piercing member via the first and second connecting pieces.

8. The device of claim 1, wherein the distal end of the piercing member including the first opening has a steep taper forming a slanted orifice to facilitate last drop withdrawal from a container having a sealing member, wherein the steep taper of the piercing member is configured for use with a variety of thicknesses of sealing members.

9. The device of claim 1, wherein the piercing member defines a longitudinal vent channel and defines a second opening at the distal end of the piercing member, the device further a body extending from the proximal end of the piercing member, the body including a first connecting portion configured to receive a mating connector and a second connecting portion configured to secure the body to a container.

10. The device of claim 9, further comprising a pressure equalization arrangement in fluid communication with the longitudinal vent channel of the piercing member.

11. The device according to claim 1, wherein the first opening of the piercing member extends longitudinally from the distal end of the piercing member.

12. A device for transferring fluids comprising:
a piercing member having a distal end and a proximal end and defining a longitudinal fluid channel, a first opening positioned at the distal end of the piercing member, the opening in fluid communication with the longitudinal fluid channel; and
a cover positioned over the first opening, the cover including a pre-cut pattern wherein the cover opens along the pre-cut pattern upon application of a distally directed force from the longitudinal fluid channel, wherein a length of the first opening of the piercing member in a direction extending from the proximal end of the piercing member to the distal end of the piercing member ensures that at least a portion of the first opening of the piercing member is located adjacent an innermost side of a sealing member of a fluid container when the piercing member has penetrated the sealing member.

13. The device according to claim 1, wherein the piercing member is cylindrical with a pointed tip at the distal end.

14. The device according to claim 13, wherein the piercing member comprises a first flat portion defining a first planar surface and a second flat portion defining a second planar surface, wherein the first and second flat portions are configured to reduce a penetration force required to pierce a sealing member of a fluid container relative to a piercing member not having the first and second flat portions.

15. A device for transferring fluids comprising:
a body having a first side and a second side;
a piercing member extending from the second side of the body, the piercing member having a distal end and a proximal end and defining a longitudinal fluid channel;
at least a first opening positioned at the distal end of the piercing member, the at least one first opening in fluid communication with the longitudinal fluid channel; and
a cover comprising a membrane that is molded over the first opening, the cover including a pre-cut pattern wherein the cover opens along the pre-cut pattern upon application of a distally directed force from the longitudinal fluid channel.

16. The device of claim 15, wherein the pre-cut pattern comprises a cut along a center portion of the cover dividing the cover into a first portion and a second portion and wherein the cover includes a first connecting piece for securing the first cover portion to a first portion of the piercing member and a second connecting piece for securing the second cover portion to a second portion of the piercing member at a location opposite from the first portion of the piercing member.

17. The device of claim 15, wherein the cover opens along the first and second connecting pieces in an outward direction with respect to the first opening and wherein the pre-cut pattern comprises a cut that partially surrounds the opening, with the exception of the first and second portions, so that the cover remains attached to the piercing member via the first and second pieces.

18. The device of claim 15, wherein the distal end of the piercing member including the first opening comprises a steep taper forming a slanted orifice to facilitate last drop withdrawal from a container having a sealing member, wherein the steep taper of the piercing member is configured for use with a variety of thicknesses of sealing members.

19. The device of claim 15, wherein the piercing member includes a longitudinal vent channel and defines a second opening at the distal end of the piercing member, the body of the device extending from the proximal end of the piercing member, the body including a first connecting portion configured to receive a mating connector and a second connecting portion configured to secure the body to a container.

* * * * *